(12) United States Patent
Vance

(10) Patent No.: US 11,801,455 B2
(45) Date of Patent: *Oct. 31, 2023

(54) SYSTEMS AND METHODS FOR REMOVING MOISTURE FROM A POWER TRANSFORMER

(71) Applicant: The Ardry Group, Rincon, GA (US)

(72) Inventor: Ed Vance, Rincon, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/112,722

(22) Filed: Feb. 22, 2023

(65) Prior Publication Data

US 2023/0264117 A1 Aug. 24, 2023

Related U.S. Application Data

(63) Continuation of application No. 17/072,275, filed on Oct. 16, 2020, now Pat. No. 11,617,967.

(60) Provisional application No. 62/956,400, filed on Jan. 2, 2020.

(51) Int. Cl.
| | |
|---|---|
| *B01D 15/10* | (2006.01) |
| *G01N 33/28* | (2006.01) |
| *H01F 27/04* | (2006.01) |
| *H01F 27/14* | (2006.01) |

(52) U.S. Cl.
CPC ......... *B01D 15/10* (2013.01); *G01N 33/2847* (2013.01); *H01F 27/14* (2013.01)

(58) Field of Classification Search
None
See application file for complete search history.

(56) References Cited

U.S. PATENT DOCUMENTS

| | | |
|---|---|---|
| 9,063,116 B2 | 6/2015 | Rasor |
| 2006/0278584 A1 | 12/2006 | Bowden et al. |
| 2014/0233605 A1 | 8/2014 | Rasor |
| 2016/0290985 A1 | 10/2016 | Roizman |

OTHER PUBLICATIONS

DryKeep, https://web.archive.org/web/20160819165701/http://www.drykeep.com/the-technology/, accessed Oct. 7, 2022, 2016.
Dalton, Tom, Moisture management of live transformers, 2008, energize, p. 30-33.

(Continued)

*Primary Examiner* — Bradley R Spies
*Assistant Examiner* — Jeannie McDermott
(74) *Attorney, Agent, or Firm* — Womble Bond Dickinson (US) LLP

(57) ABSTRACT

The disclosure includes embodiments of systems and methods for removing moisture from an electric power transformer. According to an embodiment, a moisture removal system includes a pump to move oil from the transformer into the system; one or more incoming oil moisture and temperature sensors to detect a first moisture level and temperature of oil; a processor to receive the moisture and temperature and determine an estimated paper moisture value of the insulation of the transformer, and compare the estimate to a target paper moisture value; and an overdry prevention bypass valve positioned in a first position to divert oil without drying when the estimated paper moisture value is equal to or less than the target value, and in a second position to channel oil through one or more drying cylinders when the estimated paper moisture value exceeds the target value.

23 Claims, 16 Drawing Sheets

(56) References Cited

OTHER PUBLICATIONS

Ding, Hongzhi, Griffin, Paul, An Overview of Water and Relative Saturation in Power Transformers, 2017, 19th IEEE International Conference on Dielectric Liquids (ICDL), Manchester, United Kingdom, Jun. 25-29, 2017.

SYSTEMS AND METHODS FOR REMOVING MOISTURE FROM A POWER TRANSFORMER

CROSS REFERENCE TO RELATED APPLICATIONS

This application is a continuation of U.S. Non-Provisional application Ser. No. 17/072,275, filed Oct. 16, 2020, titled "SYSTEMS AND METHODS FOR REMOVING MOISTURE FROM A POWER TRANSFORMER," which claims the benefit of and priority to U.S. Provisional Application No. 62/956,400, filed Jan. 2, 2020, titled "SYSTEMS AND METHODS FOR REMOVING MOISTURE FROM A POWER TRANSFORMER," the entire disclosures of which are incorporated herein by reference.

BACKGROUND

1. Field of Invention

The present disclosure relates generally to the power industry and, more particularly, to the field of power transformer systems and methods.

2. Description of Background

Power transformers are one of the most critical assets in the electric grid. Though most transformers have a life expectancy of 25-40 years, these crucial components may last longer with proper maintenance. Increasing transformer life expectancy is desirable, particularly given the high cost of transformer failure and replacement. Many utilities are faced with reducing capital and maintenance expenditures. Extension of the life of a power transformer is a key strategy in achieving these cost reduction goals. Although reactive asset management is inefficient and costly, proactive measures to preserve transformer soundness may be a more expedient strategy for cost savings and efficiency.

Transformers are formed primarily of copper, grain-oriented electrical steels (GOES), cellulose paper insulation, and wood, with insulating oil running therethrough. The longevity of copper and steel are not problematic, and while the oil ages more rapidly, it may easily be treated or replaced. The cellulose paper insulation, however, is particularly susceptible to degradation and aging due to changes in temperature, oxygen, acid, and moisture levels during transformer use.

SUMMARY

Applicant has recognized that although temperature, oxygen, and acids may be monitored and addressed, moisture in the cellulose insulation often tends to be left unabated, making it the single greatest reason that the cellulose inside the transformer ages, degrades, and eventually causes the transformer to fail. The cellulose insulation cannot be renewed or replaced without major cost to the owner, such that cellulose insulation preservation through proper dehydration represents a key step in extending the life of the transformer.

Moisture may enter the cellulose paper insulation through a number of different locational avenues, including residual moisture after initial factory dry-out of the cellulose, ingress from the atmosphere, aging decomposition of the cellulose, or aging decomposition of the oil. Further, during normal operation of the transformer, any increase in operating temperature will drive moisture out of the cellulose paper insulation. This free moisture will either dissolve in the oil if the oil is "dry" enough, or will "rain down," in an energized field, in the interface between the oil and the cellulose paper. Similarly, with any decrease in temperature during operation, the moisture will migrate back into the paper from the oil, but tends to do so at a much slower rate than when the moisture is driven out of the paper. Because the cellulose paper insulation has a much higher affinity for moisture than oil, the paper is more likely to absorb moisture in place of the oil.

The presence of moisture in the paper promotes acid-hydrolysis by causing carboxylic acids to dissociate, aging the paper more rapidly than if moisture were abated and more moisture formed. The aging becomes auto-acceleratory, particularly when the moisture level rises above 1.5%. Indeed, paper with 3.5% moisture degrades at a rate 20 times faster than paper with 0.5% moisture, with the presence of moisture in the transformer leading to chemical decomposition of both the paper insulation and the oil, deterioration of the dielectric properties of the paper and oil, and irreversible deterioration of the mechanical properties of the paper. This deterioration leads to insulation failure and, ultimately, transformer failure. Cellulose paper insulation deterioration accounts for 20% of all transformer failures, second only to line surges.

Yet moisture removal alone is not sufficient. Just as an abundance of moisture may cause cellulose paper insulation deterioration and may lead to premature transformer failure, overdrying may also be problematic. Power transformer windings are designed to withstand high axial forces that result from short circuit events. To withstand these forces, the winding assembly is clamped to a predetermined pre-load pressure during the manufacturing process. As long as the transformer clamping system maintains the pre-load pressure, the windings will remain tight during a short circuit event, and should prevent sustained damage to the transformer. Cellulose insulation that has absorbed moisture will swell, causing the windings to tighten. Transversely, as moisture is removed from the insulation, the swelling will subside. In the event of over-drying of the cellulose paper insulation, the insulation may shrink to a lesser thickness than its manufactured state, causing the windings to become loose, such that the windings are likely to fail to withstand the force of short circuit events. This loosening may ultimately damage the transformer.

Applicant also has recognized the difficulties noted above and that there is an unmet need for systems and methods for efficiently, effectively, and continuously removing moisture from a power transformer, in order to extend the life of the transformer, while preventing overdrying of the cellulose paper insulation in the transformer. The present disclosure is directed to systems and methods for moisture removal that provide an elegant solution to these previously unmet needs.

The moisture removal system described herein addresses the unsolved problems with cellulose paper insulation saturation and transformer failure by slowing the auto-acceleratory aging effects caused by the presence of moisture in the paper through a more effective removal of the moisture from the cellulose insulation system. This process of drying or maintaining the relative dryness of the paper insulation increases the service life and reliability of the transformer, enabling transformers to be run on higher load cycles with reduced risk of failure.

According to an embodiment, a system for removing moisture from a power transformer while the transformer remains online and energized is described. The system may include a combination of the electric power transformer and a moisture removal system. The electric power transformer may be electrically connected to an electric grid, and may have a plurality of cellulose paper insulation positioned therein and may have oil running therethrough. The moisture removal system may be fluidly connected to the electric power transformer at an input channel and an output channel. The moisture removal system may include a pump, one or more incoming moisture and temperature sensors, a processor, and an overdry prevention bypass valve. The pump may be positioned so as to move oil from the power transformer into and through the moisture removal system via the input channel. The incoming oil moisture and temperature sensors may be positioned so as to detect a first moisture level and a first temperature of oil pumped from the power transformer into the moisture removal system via the input channel. The processor may be positioned to receive the first moisture level and the first temperature from the incoming oil moisture and temperature sensors, and the processor may be configured to calculate or determine, based on the first moisture level and the first temperature, an estimated paper moisture value of the cellulose paper insulation, and may be further configured to compare the estimated paper moisture level to a predetermined target paper moisture value. The overdry prevention bypass valve may be configured to be positioned in a first position so as to divert oil to the output channel without drying when the processor determines, based on the comparing, that the estimated paper moisture value is equal to or less than the predetermined target paper moisture value, and to be positioned in a second position so as to channel oil through one or more drying cylinders so as to remove moisture from the oil when the processor determines, based on the comparing, that the estimated paper moisture value exceeds the predetermined target paper moisture value.

The system further may include an outgoing oil moisture and temperature sensor, positioned so as to detect a second moisture level and a second temperature of oil that has passed through the one or more drying cylinders before returning to the electric power transformer via the output channel. The processor may be configured to compare the first moisture level of the incoming oil with the second moisture level of the outgoing oil, and further may be configured to trigger a drying cylinder saturation alarm when the second moisture level of the outgoing oil is determined to be equal to or greater than the first moisture level of the incoming oil.

The incoming oil moisture and temperature sensors and the outgoing oil moisture and temperature sensor may be configured to detect each of the first moisture level, the second moisture level, the first temperature, and the second temperature on a continuous basis.

The system further may include a graphic user interface (GUI) connected to the incoming oil moisture and temperature sensors, outgoing oil moisture and temperature sensor, and processor, and the GUI may be configured to display data received from each of the incoming oil moisture and temperature sensor, outgoing oil moisture and temperature sensor, and processor.

The GUI may be selected from one or more of a GUI positioned on the moisture removal system and directly connected to the incoming oil moisture and temperature sensor, outgoing oil moisture and temperature sensor, and processor, and a GUI positioned remotely from the moisture removal system and wired or wirelessly connected to the incoming oil moisture and temperature sensor, outgoing oil moisture and temperature sensor, and processor via a remote network.

The GUI may be configured to receive an input at the GUI and communicate, via the processor, a command to move the overdry prevention bypass valve to one of the first position and the second position based on the received input.

The one or more drying cylinders may include zeolite granules positioned to capture water moisture molecules from the oil as the oil passes through the one or more drying cylinders.

The present disclosure also is directed to a system for removing moisture from an electric power transformer. According to an embodiment, the system may include an input channel, a pump, an incoming oil moisture and temperature sensor, a processor, an output channel, and an overdry prevention bypass valve. The input channel may be positioned to remove incoming oil received from the electric power transformer, the electric power transformer positioned to be in fluid communication with the system and having a plurality of cellulose paper insulation positioned therein and having oil running therethrough. The pump may be positioned so as to move oil from the electric power transformer into and through the moisture removal system via the input channel. The incoming oil moisture and temperature sensors may be positioned so as to detect a first moisture level and a first temperature of oil pumped from the electric power transformer into the moisture removal system via the input channel. The processor may be positioned to receive the first moisture level and the first temperature from the incoming oil moisture and temperature sensors, the processor configured to calculate or determine, based on the first moisture level and the first temperature, an estimated paper moisture value of the cellulose paper insulation, and further configured to compare the estimated paper moisture value to a predetermined target paper moisture value. The output channel may be positioned to return oil from the system to the electric power transformer. The overdry prevention bypass valve may be configured to be positioned in a first position so as to divert oil to the output channel without drying when the processor determines, based on the comparing, that the estimated paper moisture level is equal to or less than the predetermined target paper moisture value, and to be positioned in a second position so as to channel oil through one or more drying cylinders so as to remove moisture from the oil when the processor determines, based on the comparing, that the estimated paper moisture value exceeds the predetermined target paper moisture value.

The system additionally may include an outgoing oil moisture and temperature sensor, positioned so as to detect a second moisture level and a second temperature of oil that has passed through the one or more drying cylinders before returning to the electric power transformer via the output channel. The processor may be configured to compare the first moisture level of the incoming oil with the second moisture level of the outgoing oil. The processor further may be configured to trigger a drying cylinder saturation alarm when the second moisture level of the outgoing oil is determined to be equal to or greater than the first moisture level of the incoming oil.

The incoming oil moisture and temperature sensors and the outgoing oil moisture and temperature sensor may be configured to detect each of the first moisture level, the second moisture level, the first temperature, and the second temperature on a continuous basis.

The system additionally may include a graphic user interface (GUI) connected to the incoming oil moisture and temperature sensors, outgoing oil moisture and temperature sensor, and processor, and may be configured to display data received from each of the incoming oil moisture and temperature sensors, outgoing oil moisture and temperature sensor, and processor.

The GUI may be selected from one or more of a GUI positioned on the moisture removal system and directly connected to the incoming oil moisture and temperature sensor, outgoing oil moisture and temperature sensor, and processor, and a GUI positioned remotely from the moisture removal system and wired or wirelessly connected to the incoming oil moisture and temperature sensors, outgoing oil moisture and temperature sensor, and processor via a remote network.

The GUI may be configured to receive an input at the GUI and communicate, via the processor, a command to move the overdry prevention bypass valve to one of the first position and the second position based on the received input.

The one or more drying cylinders may include zeolite granules positioned to capture water moisture molecules from the oil as the oil passes through the one or more drying cylinders.

An embodiment of a system to remove moisture from a power transformer may also include a power transformer electrically connected to an electric grid. The power transformer may have cellulose paper insulation, for example, positioned therein and having oil running therethrough. The embodiment may also include a moisture removal system fluidly connected to the power transformer at an input channel and an output channel and positioned to move the oil from and to the power transformer. The moisture removal system, for example, may include a pump positioned so as to move oil from the power transformer into and through the moisture removal system through the input channel from the power transformer and return to the power transformer through the output channel, an internal moisture removal conduit fluidly connected to the input channel to receive the oil therefrom and fluidly connected to the output channel to return oil thereto, the internal moisture removal conduit including a first internal conduit path and a second internal conduit path, one or more drying cylinders fluidly connected to the first internal conduit path to reduce moisture content of the oil when flowing therethrough, one or more incoming oil moisture and temperature sensors positioned so as to detect moisture level and temperature of the oil when pumped from the power transformer into the moisture removal system through the input channel, and a controller positioned to receive the detected moisture level and temperature from the incoming oil moisture and temperature sensors. The controller may be responsive to the detected moisture level and temperature to determine an estimated paper moisture value of the cellulose paper insulation and to compare the determined estimated paper moisture value to a preselected target paper moisture value. The moisture removal system further may include an overdry prevention bypass valve responsive to the controller to direct the flow of the oil between the first internal conduit path and the second internal conduit path and positioned so as to allow the oil to circulate through the first internal conduit path to the one or more drying cylinders to reduce moisture content in the oil and to the output channel therefrom when the estimated paper moisture value is greater than the preselected target paper moisture value and to divert oil through the second internal conduit path directly to the output channel without substantively reducing the moisture content in the oil when the estimated paper moisture value is equal to or less than the preselected target paper moisture value.

The present disclosure also is directed to a method for removing moisture from an electric power transformer. According to an embodiment, the method may include fluidly connecting a moisture removal system with an electric power transformer at an input channel and an output channel, the electric power transformer electrically connected to an electric grid and having a plurality of cellulose paper insulation therein and oil running therethrough; pumping oil from the electric power transformer into the moisture removal system via the input channel; detecting a first moisture level and a first temperature of the incoming oil with one or more incoming oil moisture and temperature sensors; calculating, via a processor, an estimated paper moisture value of the cellulose paper insulation based at least in part on the detected first moisture level and the first temperature of the incoming oil; comparing, via the processor, the estimated paper moisture value to a predetermined target paper moisture value; and positioning, via the processor, an overdry prevention bypass valve based at least on the comparing, the overdry prevention bypass valve configured to be positioned to channel the incoming oil through one or more drying cylinders positioned to remove moisture from the oil when the estimated paper moisture value is determined to be greater than the predetermined target paper moisture value, and configured to be positioned to divert the incoming oil to bypass the one or more drying cylinders when the estimated paper moisture value is determined to be less than or equal to the predetermined target paper moisture value.

The method further may include detecting a second moisture level of the outgoing oil with an outgoing oil moisture and temperature sensor after the oil passes through the one or more drying cylinders; comparing, via the processor, the first moisture level of the incoming oil with the second moisture level of the outgoing oil; determining, via the processor, that second moisture level of the outgoing oil is equal to or greater than the first moisture level of the incoming oil; and triggering a drying cylinder saturation alarm, via the processor, based at least in part on the determining.

The incoming oil moisture and temperature sensors and the outgoing oil moisture and temperature sensor may be configured to detect each of the first moisture level, the second moisture level, the first temperature, and the second temperature on a continuous basis.

The method further may include displaying data received from each of the incoming oil moisture and temperature sensors, outgoing oil moisture and temperature sensor, and processor on a graphic user interface (GUI) connected to each of the incoming oil moisture and temperature sensors, outgoing oil moisture and temperature sensor, and processor.

Displaying data received from each of the incoming oil moisture and temperature sensor, outgoing oil moisture and temperature sensor, and processor on the GUI may include one or more of displaying data at a GUI positioned on the moisture removal system and directly connected to the incoming oil moisture and temperature sensor, outgoing oil moisture and temperature sensor, and processor, and displaying data at a GUI positioned remotely from the moisture removal system and wired or wirelessly connected to the incoming oil moisture and temperature sensor, outgoing oil moisture and temperature sensor, and processor via a remote network.

The method further may include receiving an input at the GUI, and communicating, via the processor, a command to move the overdry prevention bypass valve to one of the first position and the second position based on the received input.

BRIEF DESCRIPTION OF DRAWINGS

Some of the features and benefits of the present disclosure having been stated, others will become apparent as the description proceeds when taken in conjunction with the accompanying drawings, in which.

While the disclosure will be described in connection with the various embodiments, it will be understood that it is not intended to limit the disclosure to that embodiment. On the contrary, it is intended to cover all alternatives, modifications, and equivalents, as may be included within the spirit and scope of the disclosure as defined by the appended claims.

DETAILED DESCRIPTION

The foregoing aspects, features, and advantages of the present disclosure will be further appreciated when considered with reference to the following description of the following embodiments and accompanying drawings. In describing the following embodiments of the disclosure illustrated in the appended drawings, specific terminology will be used for the sake of clarity. The disclosure, however, is not intended to be limited to the specific terms used, and it is to be understood that each specific term includes equivalents that operate in a similar manner to accomplish a similar purpose. Numerous specific details, examples, and embodiments are set forth and described to provide a thorough understanding of various embodiments of the present invention. In certain instances, however, well-known or conventional details may not be described in order to provide a concise discussion of embodiments of the present disclosure.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. Any examples of operating parameters and/or environmental conditions are not exclusive of other parameters/conditions of the disclosed embodiments. Additionally, it should be understood that references to "one embodiment," "an embodiment," "certain embodiments," or "other embodiments" of the present disclosure are not intended to be interpreted as excluding the existence of additional embodiments that also incorporate the recited features. Furthermore, reference to terms such as "above," "below," "upper," "lower," "side," "front," "back," or other terms regarding orientation are made with reference to the illustrated embodiments and are not intended to be limiting or exclude other orientations.

Figure 1:
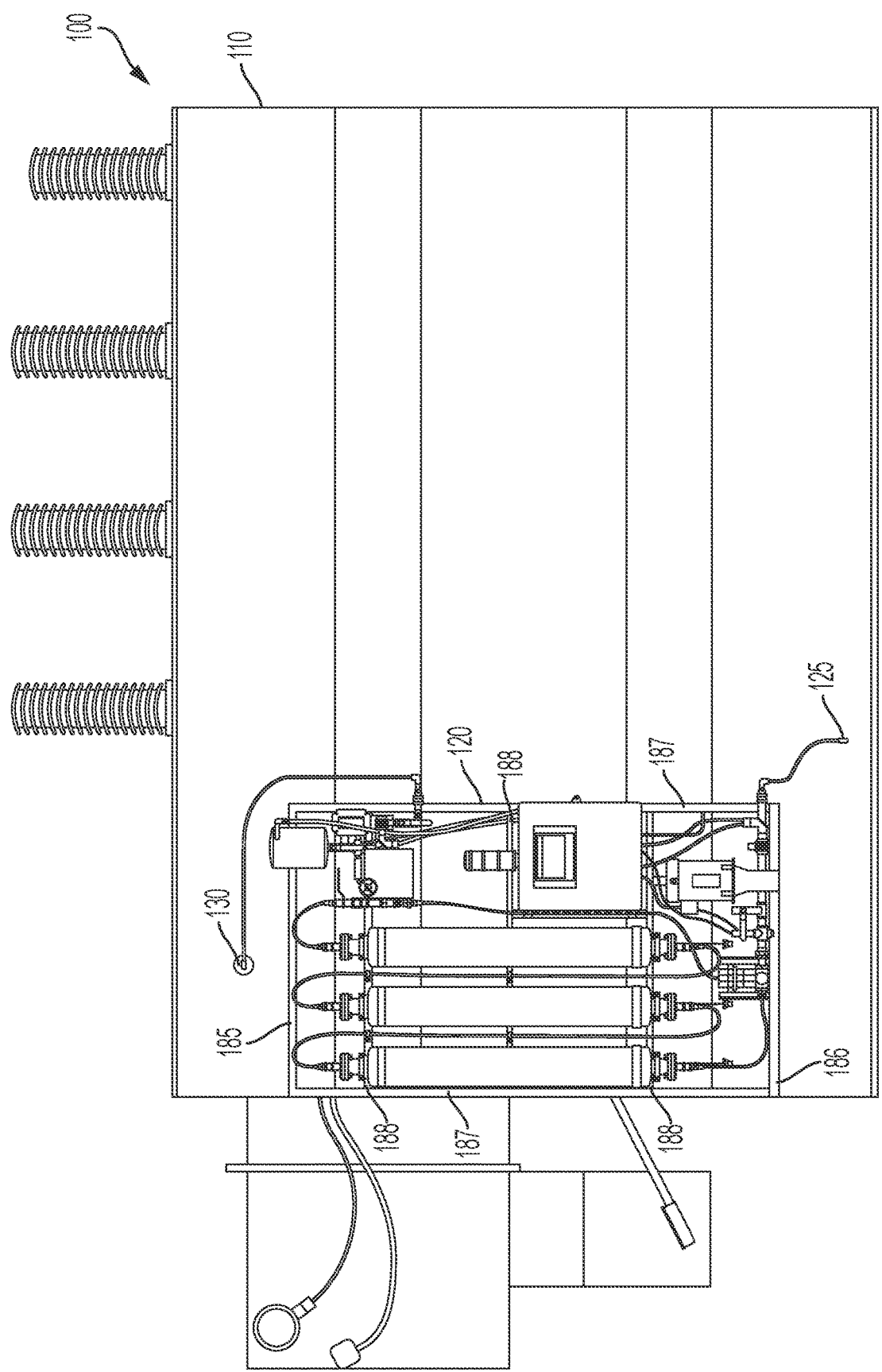
FIG. 1 is a diagram of a system for removing moisture from an electric power transformer, according to an embodiment.

The present disclosure is directed to systems and methods for removing moisture from an electric power transformer. According to an embodiment, a system 100 for removing moisture from an electric power transformer 110, as illustrated in FIG. 1, is described. The system 100 may include the electric power transformer 110, which may be electrically connected to an electric grid. The electric power transformer 110 may have a plurality of cellulose paper insulation positioned therein, and may have oil running therethrough. The system 100 may additionally include a moisture removal system 120 fluidly connected to the electric power transformer 110 via an input channel 125 and an output channel 130.

As illustrated in the embodiment according to FIG. 2, the moisture removal system 120 may include a pump 135 positioned so as to move oil from the electric power transformer 110 into and through the moisture removal system 120 via the input channel 125. The pump 135 may be the only active component of the moisture removal system 120, such that fluidly connecting the moisture removal system 120 to the electric power transformer 110 presents no electrical risk to the electric power transformer 110. In the event that a problem is detected in the operation of the moisture removal system 120, the system 120 may automatically shut off the pump 135 and close a plurality of isolation safety valves in order to completely isolate the system 120 from the electric power transformer 110, avoiding any potential damage to the electric power transformer 110.

The moisture removal system 120 also may include one or more incoming moisture and temperature sensors 140, positioned so as to detect a first moisture level and a first temperature of oil pumped from the electric power transformer 110 into the moisture removal system 120 via the input channel 125. In some embodiments, the incoming moisture and temperature sensors 140 may be a Vaisala HUMICAP® MMT162 moisture-in-oil sensors, designed to read the parts-per-million (PPM) of moisture in the oil, percent relative saturation of oil, and the oil temperature. The incoming moisture and temperature sensors 140 may continuously measure the water content and temperature of the oil entering the moisture removal system 120 so as to prevent both over-saturation and over-drying of the cellulose paper insulation in the electric power transformer 110. As water solubility may be dependent on the temperature of oil, the incoming moisture and temperature sensors 140 may continuously measure the percent relative saturation of the oil. The percent relative saturation of the oil may include a ratio of the actual water content of the oil to the maximum water content the oil holds at the measured temperature.

The moisture removal system 120 also may include a processor 145 positioned to receive the first moisture level, the first temperature, and/or the first percent relative saturation of incoming oil from the incoming oil moisture and temperature sensors 140. The processor 145 may be configured to calculate or determine, based on the first moisture level, the first temperature, and/or the first percent relative saturation of incoming oil, an estimated paper moisture value of the cellulose paper insulation, and may further be configured to compare the estimated paper moisture value to a predetermined target paper moisture value. By directly measuring the temperature and moisture level, as well as the percent relative saturation, of the incoming oil, the incoming oil moisture and temperature sensors 140 may communicate that data to the processor 145 so that the processor 145 may derive, and thereby indirectly calculate or determine, the moisture level of the cellulose paper insulation in the electric power transformer 110. The processor 145 may use the real-time data from the incoming oil moisture and temperature sensors 140 to control the drying process, communicate data to a graphic user interface (GUI) for use by responsible personnel, log historical data, and provide trend analysis. For example, the processor 145 may calculate or determine the percent moisture in the cellulose paper insulation of the electric power transformer 110 by using an algorithm to convert the oil moisture and temperature data received from the incoming oil moisture and temperature sensors 140 into an estimated percentage moisture level of the cellulose paper insulation. For example, as shown below in Table 1, where the incoming oil moisture and temperature sensors 140 detects an oil temperature of 45 degrees Celsius and an oil moisture level of 37 PPM, the processor 145 will calculate or determine an estimated paper moisture of 4.25%. In another example, the incoming oil moisture and temperature sensors 140 may detect a percent relative saturation of the oil, rather than or in addition to the oil moisture level, and the oil temperature. In such examples, the processor 145 may utilize the percent relative saturation of the oil, rather than or in addition to the oil moisture level, and oil temperature to calculate or determine the estimated percentage moisture level of the cellulose paper insulation.

TABLE 1

Transformer Insulation Moisture Estimation Using PPM Measurements

| Oil temperature (° C.) | Oil moisture (PPM) | Cellulose paper insulation moisture (%) |
|---|---|---|
| 45 | 37.00 | 4.250 |
| 27 | 44.00 | 8.511 |
| 44 | 18.00 | 2.948 |
| 23 | 13.00 | 4.640 |
| 59 | 24.00 | 2.248 |
| 33 | 22.00 | 4.508 |
| 37 | 31.00 | 4.896 |
| 38 | 22.00 | 3.916 |
| 54 | 17.00 | 2.160 |
| 23 | 14.00 | 4.844 |
| 23 | 4.00 | 2.378 |
| 20 | 3.00 | 2.180 |
| 28 | 3.00 | 1.688 |
| 50 | 23.00 | 2.840 |
| 38 | 20.00 | 3.708 |
| 23 | 8.00 | 3.490 |
| 22 | 7.00 | 3.376 |

Figure 7B:
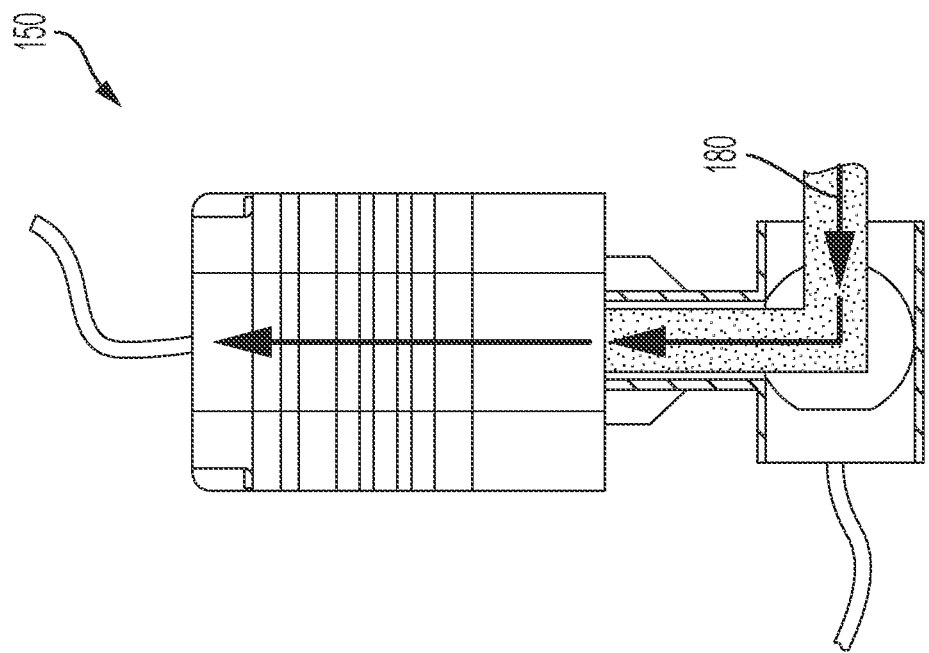
FIG. 7B is a partial detail view of an overdry prevention bypass valve and oil flow therethrough, according to another embodiment.
Figure 7A:
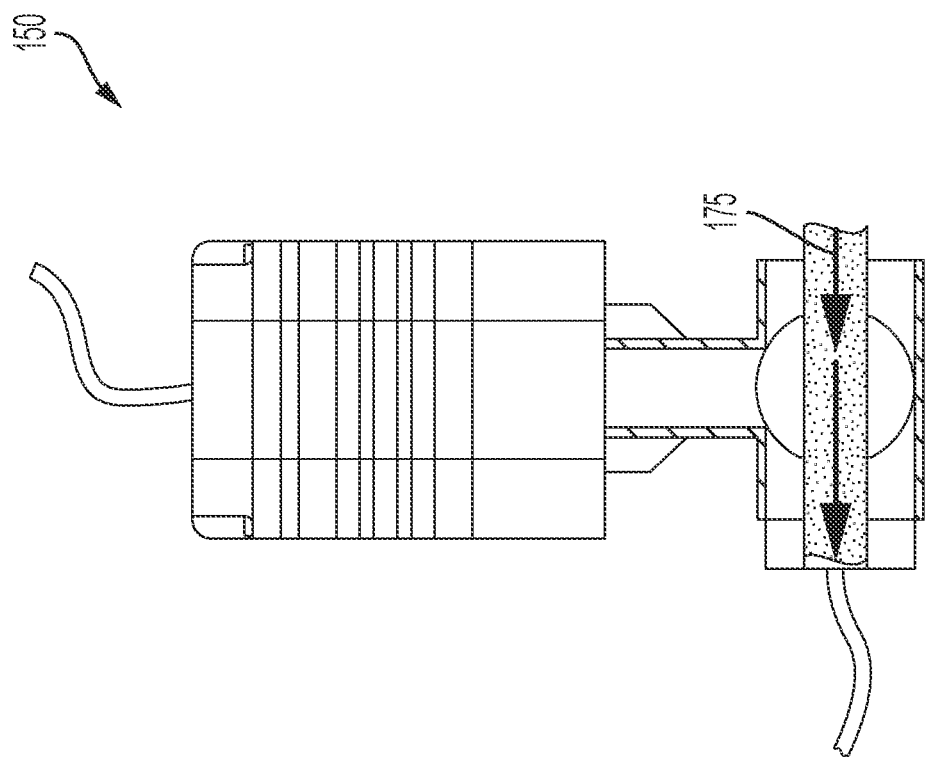
FIG. 7A is a partial detail view of an overdry prevention bypass valve and oil flow therethrough, according to an embodiment.

The moisture removal system 120 may also include an overdry prevention bypass valve 150. As illustrated in more detail in FIGS. 7A and 7B, the overdry prevention bypass valve 150 may be configured to be positioned in a first position (FIG. 7B) to channel oil so as to bypass one or more drying cylinders 155a, 155b, 155c, or a second position (FIG. 7A) to channel oil through the one or more drying cylinders 155a, 155b, 155c, based on a signal received from the processor 145. For example, the processor 145 received moisture and temperature data from the incoming oil moisture and temperature sensors 140, and derive an estimated paper moisture value. The processor 145 may then compare the estimated paper moisture value to a predetermine target paper moisture value. If the processor 145 determines, based on the comparing, that the estimated paper moisture value is equal to or less than the predetermined target paper moisture value, for example, the processor 145 may communicate a signal to the overdry prevention bypass valve 150 to position the valve 150 in the first position so as to bypass the one or more drying cylinders 155a, 155b, 155c. In other words, the processor 145 has determined that the cellulose paper insulation does not contain more moisture than may be desired, and therefore no drying of the oil is necessary. In the alternative, if the processor 145 determines, based on the comparing, that the estimated paper moisture value is greater than the predetermined target paper moisture value, the processor 145 may communicate a signal to the overdry prevention bypass valve 150 to position the valve 150 in the second position so as to channel the oil through the one or more drying cylinders 155a, 155b, 155c so as to remove the excess moisture from the oil.

Figure 2A:
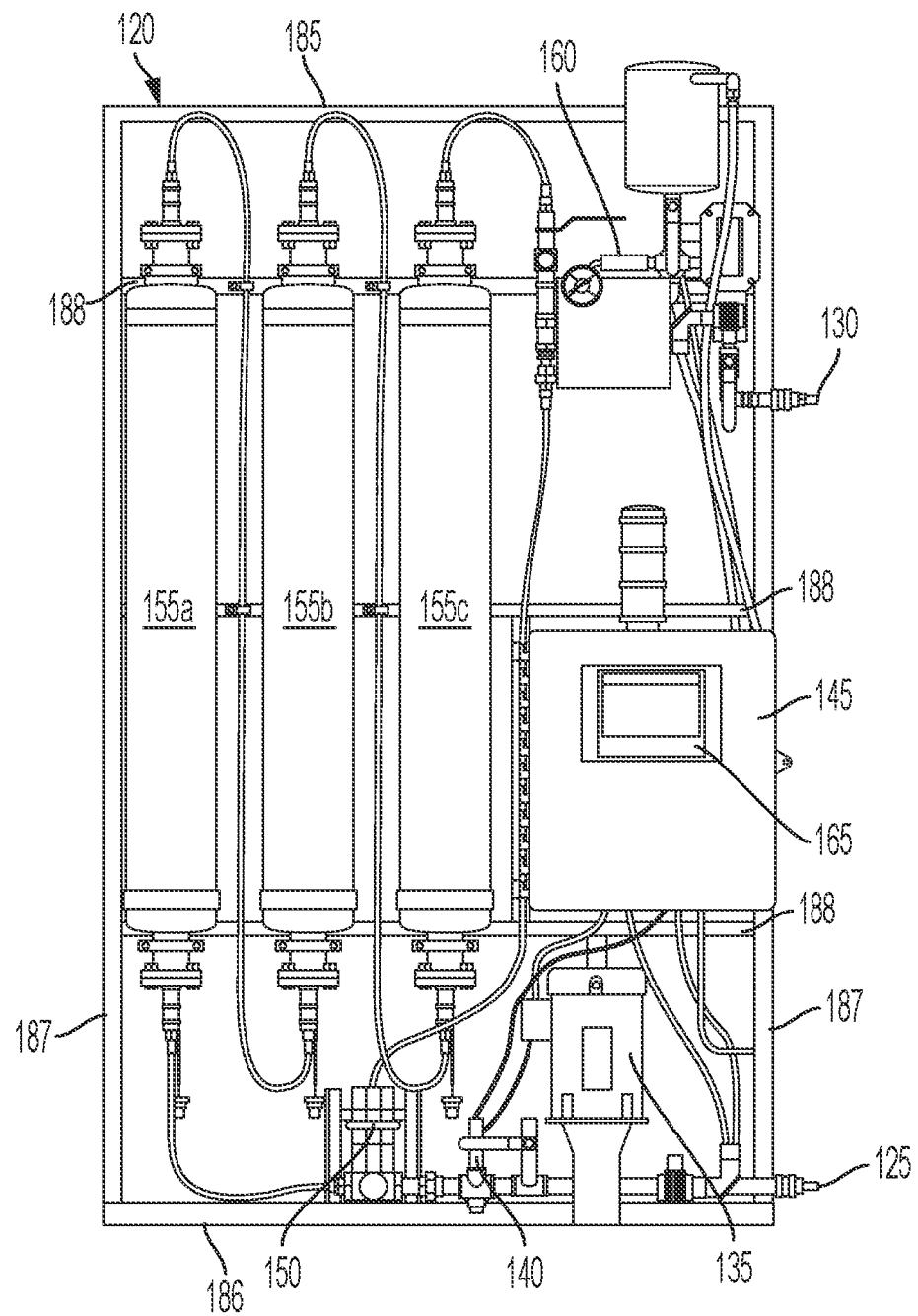
FIGS. 2A through 2B are detailed views of a moisture removal system, according to an embodiment.
Figure 2B:
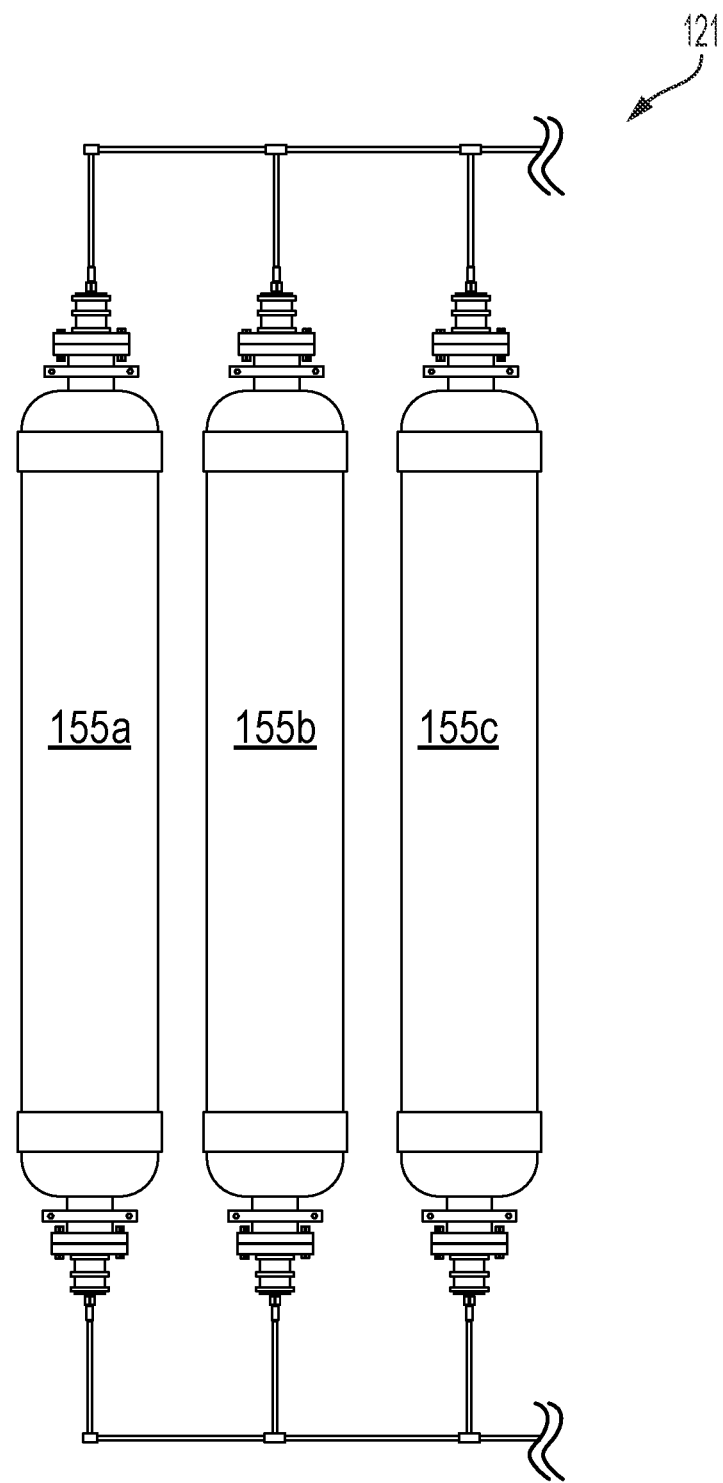

The one or more drying cylinders 155a, 155b, 155c of the moisture removal system 120 may be positioned in series (as illustrated by FIG. 2A) or in parallel (as illustrated by FIG. 2B and the set of drying cylinders 121), and may contain zeolite granules to capture and bind the moisture contained in the oil as the oil passes through the cylinders 155a, 155b, 155c, according to some embodiments, though different materials suitable for removing moisture from oil are also contemplated according to various other embodiments. Although illustrated having three drying cylinders 155a, 155b, 155c, other embodiments are contemplated in which one, two, four, or more drying cylinders are used. By removing moisture from the oil, the moisture removal system 120 allows for indirect drying of the cellulose paper insulation because the oil from which the moisture has been removed may be more capable of receiving moisture collected in the cellulose paper insulation. By contrast, oil with a higher moisture content may be less capable of receiving additional moisture, and, therefore, may be less able to draw excess moisture out of the cellulose paper insulation.

The moisture removal system 120 may be a kit (e.g., a system, separate from the electric power transformer 110, to add to an electric power transformer 110). In such examples, the moisture removal system 120 may be added to a new or an existing/currently operating electric power transformer 110. In other words, the moisture removal system 120 may be added to or removed from an electric power transformer 110 during, prior to, or after ceasing operation of the electric power transformer 110. While the moisture removal system 120 may be added to an operating and energized electric power transformer 110, to ensure safety (e.g., a low to no risk of electrocution of personnel installing the moisture removal system 120), the electric power transformer 110 may be de-energized prior to installation or removal. Installation of the moisture removal system 120 may include attaching, via apertures or attachment features disposed on the top section 185, bottom section 186, side sections 187, and cross sections 188 of the frame of the moisture removal system 120, directly to an electric power transformer 110, to a wall nearby the electric power transformer 110, or to any other structure or free-standing frame nearby the electric power transformer 110.

Figure 3:
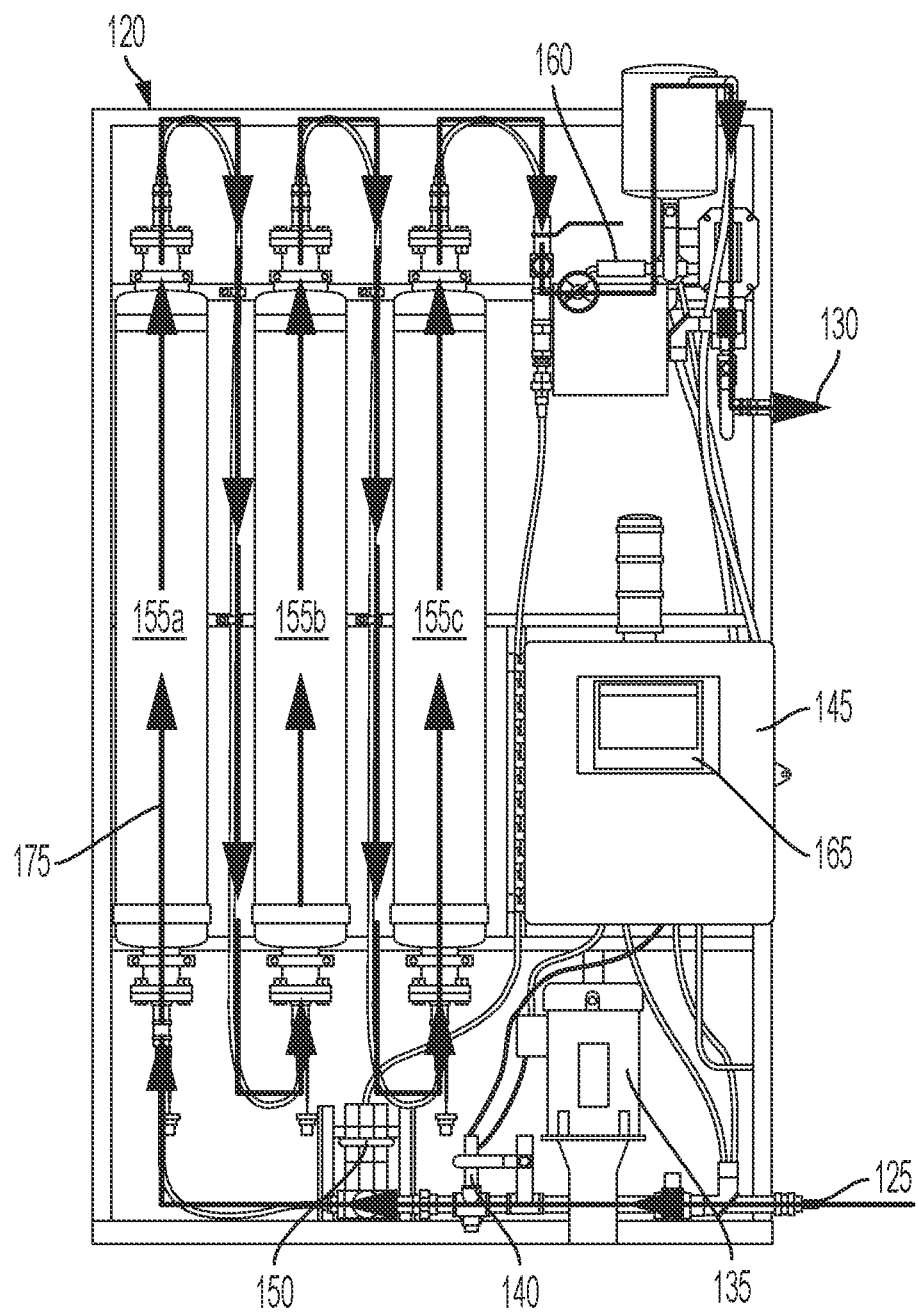
FIG. 3 is a flow diagram of oil flow through a moisture removal system, according to an embodiment.
Figure 4:
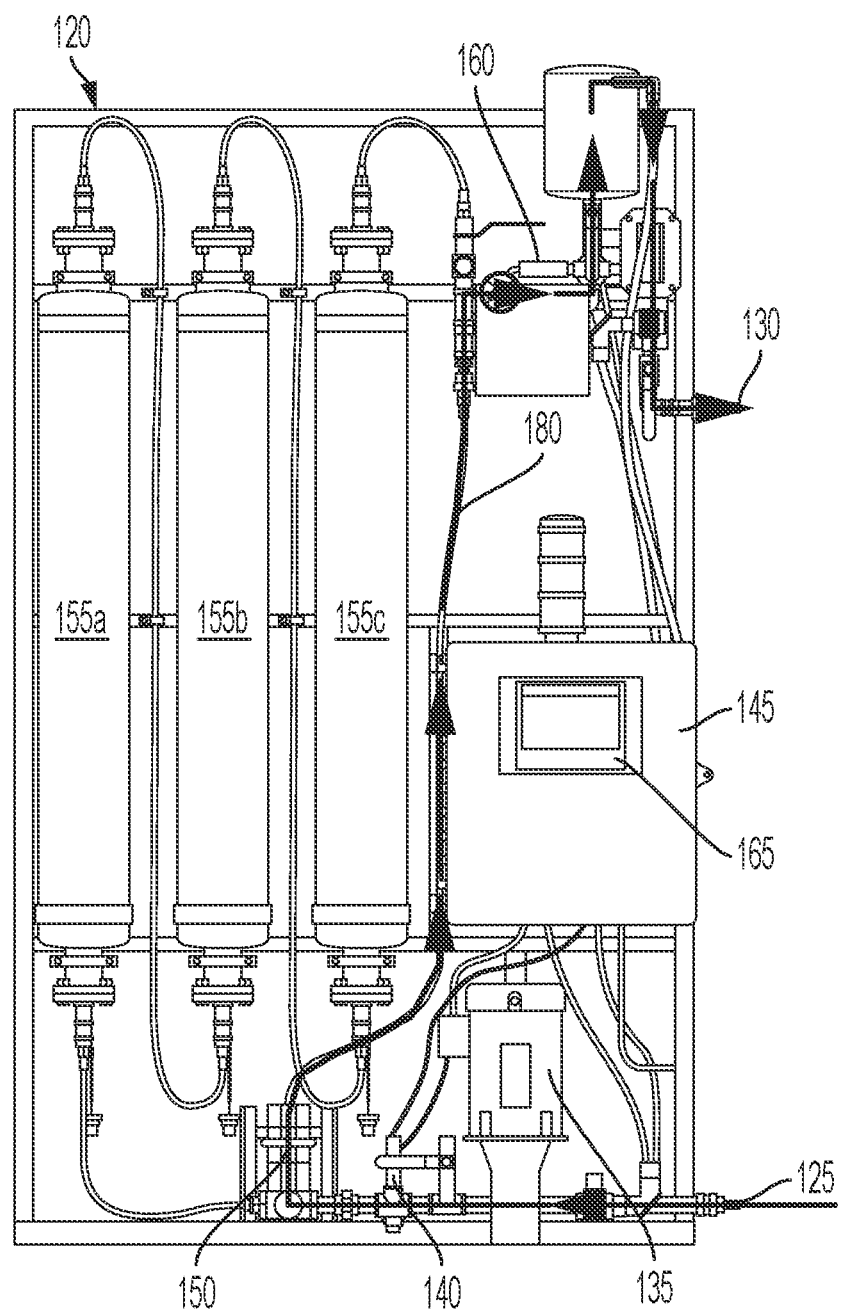
FIG. 4 is a flow diagram of oil flow through a moisture removal system, according to another embodiment.

FIGS. 3 and 4 illustrate example flow paths of oil based on the first position and second position of the overdry prevention bypass valve 150, according to embodiments. For example, in FIG. 3, the overdry prevention bypass valve 150 is positioned in the second position so as to channel the oil along a path 175 leading through each of the drying cylinders 155a, 155b, 155c so as to remove excess moisture from the oil. After passing through the drying cylinders 155a, 155b, 155c, the oil is returned to the electric power transformer 110 via the output channel 130. The overdry prevention bypass valve 150 may be positioned in the second position based on a signal received from the processor 145, after the processor has calculated or determined the estimated paper moisture value from the oil moisture and temperature data received from the incoming oil moisture and temperature sensors 140 and compared the estimated paper moisture value to the target paper moisture value, and determined that the estimated paper moisture value exceeds the target paper moisture value, such that moisture removal may be necessary.

In the embodiment illustrated in FIG. 4, the overdry prevention bypass valve 150 is positioned in the first position so as to channel the oil along a path 180 to bypass the drying cylinders 155a, 155b, 155c and return the oil to the electric power transformer 110 via the output channel 130. The overdry prevention bypass valve 150 may be positioned in the first position based on a signal received from the processor 145, after the processor has calculated determined the estimated paper moisture value from the oil moisture and temperature data received from the incoming oil moisture and temperature sensors 140 and compared the estimated paper moisture value to the target paper moisture value, and determined that the estimated paper moisture value may be less than or equal to the target paper moisture value, such that moisture removal may be unnecessary.

The moisture removal system 120 may additionally include an outgoing oil moisture and temperature sensor 160 or sensors, positioned so as to detect a second moisture level, a second percent relative saturation of the oil, and/or a second temperature of oil that has passed through the one or more drying cylinders 155a, 155b, 155c before returning to the electric power transformer 110 via the output channel 130. Like the incoming oil moisture and temperature sensors 140, the outgoing oil moisture and temperature sensor 160 may be a Vaisala HUMICAP® MMT162 moisture-in-oil sensor, designed to read the parts-per-million (PPM) of moisture in the oil, percent relative saturation of the oil, and the oil temperature. This sensor 160 may continuously measure the water content and temperature of the oil exiting the moisture removal system 120 so as to prevent both over-saturation and over-drying of the cellulose paper insulation in the electric power transformer 110.

The processor 145 may be configured to receive data indicating a second oil moisture level and/or second oil percent relative saturation from the outgoing oil moisture and temperature sensor 160, and compare that second oil moisture level and/or second oil percent relative saturation with the first moisture level data and/or first oil percent relative saturation data, respectively, received from the first oil moisture and temperature sensors 140. Based on the comparing, the processor 145 may be configured to trigger a drying cylinder saturation alarm when the second moisture level and/or second percent relative saturation of the outgoing oil is determined to be equal to or greater than the first moisture level and/or first percent relative saturation, respectively, of the incoming oil. If the moisture level and/or percent relative saturation of the outgoing oil, after being channeled through the drying cylinders 155a, 155b, 155c, is equal to or greater than the moisture level and/or percent relative saturation, respectively, of the incoming oil, it is apparent that the drying cylinders 155a, 155b, 155c are fully saturated with previously removed moisture, and are no longer capable of removing moisture from the oil being channeled through the drying cylinders 155a, 155b, 155c. By triggering the drying cylinder saturation alarm, personnel may be notified of this condition and may take action to replace the drying cylinders 155a, 155b, 155c or the drying material therein.

Figure 5:
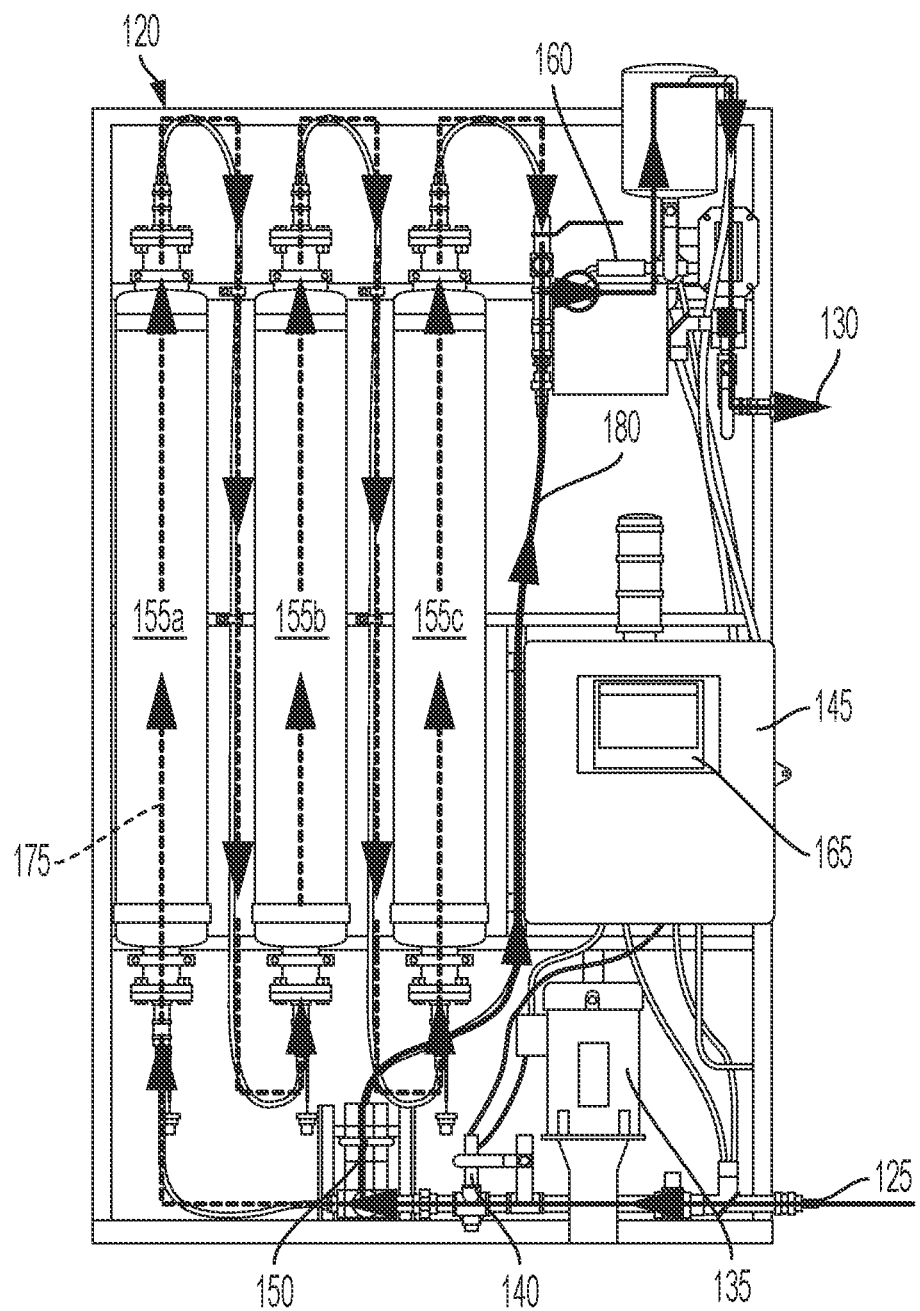
FIG. 5 is a flow diagram of oil flow through a moisture removal system, according to another embodiment.

By continuously channeling oil through the moisture removal system 120, and continuously monitoring the incoming oil moisture, percent relative saturation, and/or temperature and outgoing oil moisture, percent relative saturation, and/or temperature using the incoming oil moisture and temperature sensors 140 and outgoing oil moisture and temperature sensor 160, respectively, the moisture removal system 120, via the processor 145, may be directly maintain a desired oil moisture level, and thereby indirectly maintain a desired cellulose paper insulation moisture level. In some examples, the processor may have determined, based on receiving the oil moisture level and temperature detected by the incoming oil moisture and temperature sensors 140 and calculating or determining an estimated paper moisture value, that the estimated paper moisture value may be less than or equal to the predetermined target paper moisture value, and may have directed the overdry prevention bypass valve 150 to be positioned in the first position so as to divert oil to the output channel 130 without drying, as illustrated, for example, in FIG. 5. The oil may be returned to the electric power transformer 110 via the output channel 130, and may cycle through the electric power transformer 110 and the moisture removal system 120 via the bypass flow channel 180 any number of times. Because the incoming oil moisture and temperature sensors 140 are continuously monitoring the incoming oil moisture level, percent relative saturation, and/or temperature, at various points in time throughout the cycling, the processor 145 may determine, based on the incoming oil moisture level, percent relative saturation, and/or temperature data received from the incoming oil moisture and temperature sensors 140, that the estimated paper moisture value of the cellulose paper insulation has increased to exceed the target paper moisture value. Based on this determination, the processor 145 may communicate a signal to the overdry prevention bypass valve 150 to switch from the first position, diverting oil along the bypass flow path 180 to exit the moisture removal system 120 without drying, to the second position, to channel the oil along the flow path 175 to remove moisture from the oil in the one or more drying cylinders 155a, 155b, 155c, as illustrated in the embodiment shown in FIG. 5. In this way, the target paper moisture value may be maintained on a continuous basis.

Figure 6:
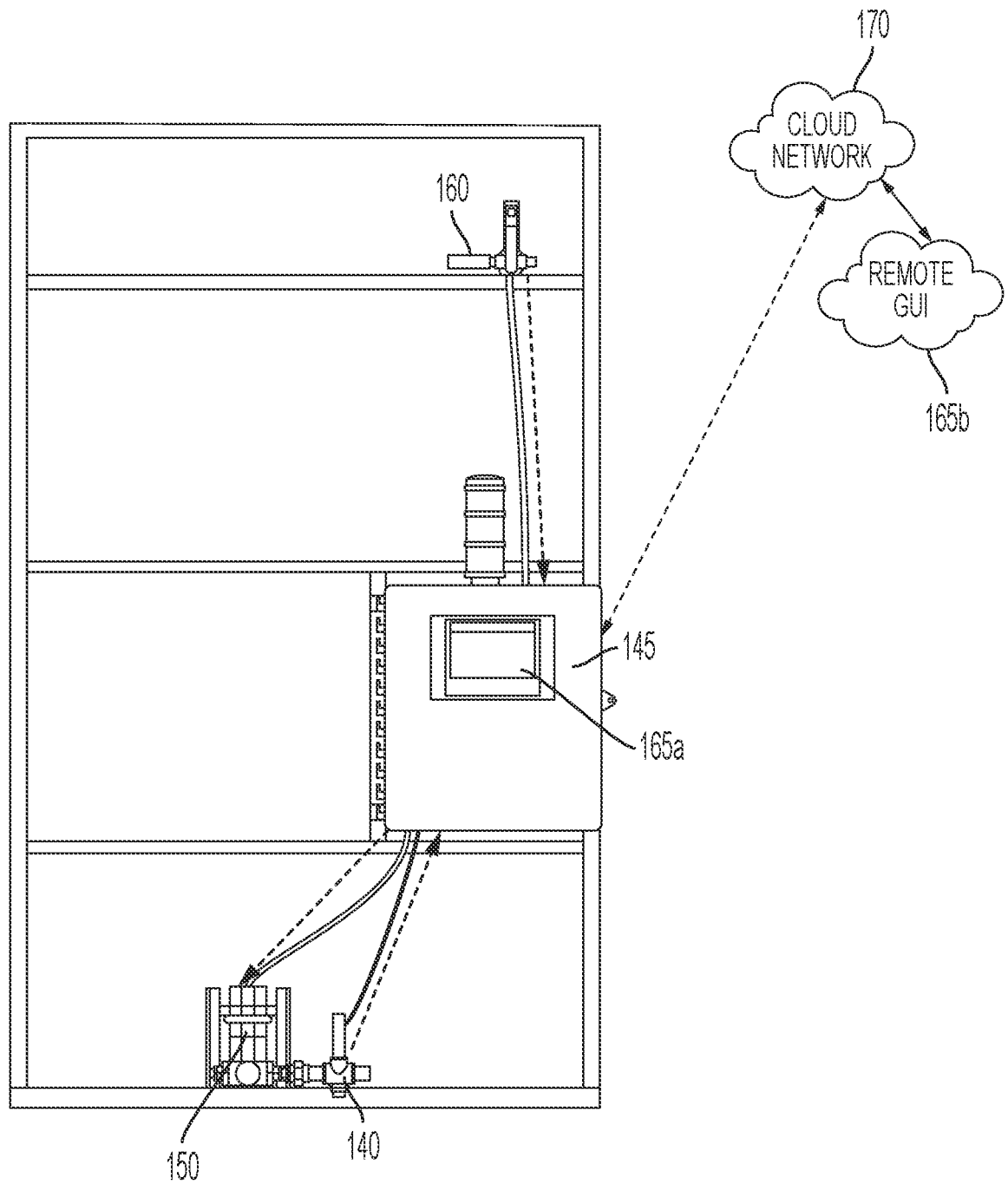
FIG. 6 is a partial diagram of a system for removing moisture from an electric power transformer, according to an embodiment.

The processor 145 may be configured to operate automatically and autonomously to receive oil moisture, percent relative saturation, and temperature data, calculate or determine estimated paper moisture values, compare estimated paper moisture values to predetermined target paper moisture values, and communicate signals to the overdry prevention bypass valve 150 based on the comparing. However, the moisture removal system 120 may also include a graphic user interface (GUI) 165, connected to the incoming oil moisture and temperature sensors 140, outgoing oil moisture and temperature sensor 160, and processor 145, and configured to display data received from each of the incoming oil moisture and temperature sensors 140, outgoing oil moisture and temperature sensor 160, and processor 145 for use by personnel, according to an embodiment. In some examples, the GUI 165a may be positioned on the moisture removal system 120 and may be directly connected to the incoming oil moisture and temperature sensors 140, outgoing oil moisture and temperature sensor 160, and processor 145. In other examples, the GUI 165b additionally or alternatively may be positioned remotely from the moisture removal system 120 and wired or wirelessly connected to the incoming oil moisture and temperature sensors 140, outgoing oil moisture and temperature sensor 160, and processor 145 via a remote network 170, as illustrated in the embodiment shown in FIG. 6. As noted, the GUI 165b may be remotely positioned from the moisture removal system 120. In such examples, the moisture removal system 120 may include data ports (e.g., Ethernet or fiber optic cable ports). The cable (e.g., Ethernet or fiber optic) may connect the data ports to a device (e.g., a computing device, such as a server, desktop or laptop) or a networking device (e.g., a switch, access point, or other device as will be understood by those skilled in the art). As such, the GUI 165b may be included on the device, may be the device, or may receive data via the networking device. In another example, the moisture removal system 120 may be capable of transmitting signals wirelessly (e.g., wirelessly connected), such as via wireless local area network (WLAN), cellular, WiFi, or other wireless connections as will be understood by those skilled in the art. Such signals may provide data from the moisture removal system 120 to GUI 165b. The GUI 165a, 165b may be configured to display data collected from the incoming oil moisture and temperature sensors 140, outgoing oil moisture and temperature sensor 160, and processor 145, as well as calculations, determinations, estimations, and alarms derived therefrom. For example, the processor 145 may be configured to receive data from each of the incoming oil moisture and temperature sensors 140 and the outgoing oil moisture and temperature sensor 160, and communicate that data to the local GUI 165a and on to the remote GUI 165b via the cloud network 170. The overdry prevention bypass valve 140 may receive commands from the local GUI 165a via the processor 145, and may additionally or alternatively receive commands from the remote GUI 165b via the cloud network 170 and the processor 145.

In an example, the GUI 165a may include a physical display (e.g., a monitor or terminal). Further, the GUI 165a may include memory storing instructions, the instructions executable by the processor 145. Instructions may include the functions or processes described herein. For example, the instructions may include instructions to display the data described herein on the physical display, as well as on any remote devices (e.g., computers, servers, tablets, smartphones, and other devices as will be understood by those skilled in the art).

Figure 8:
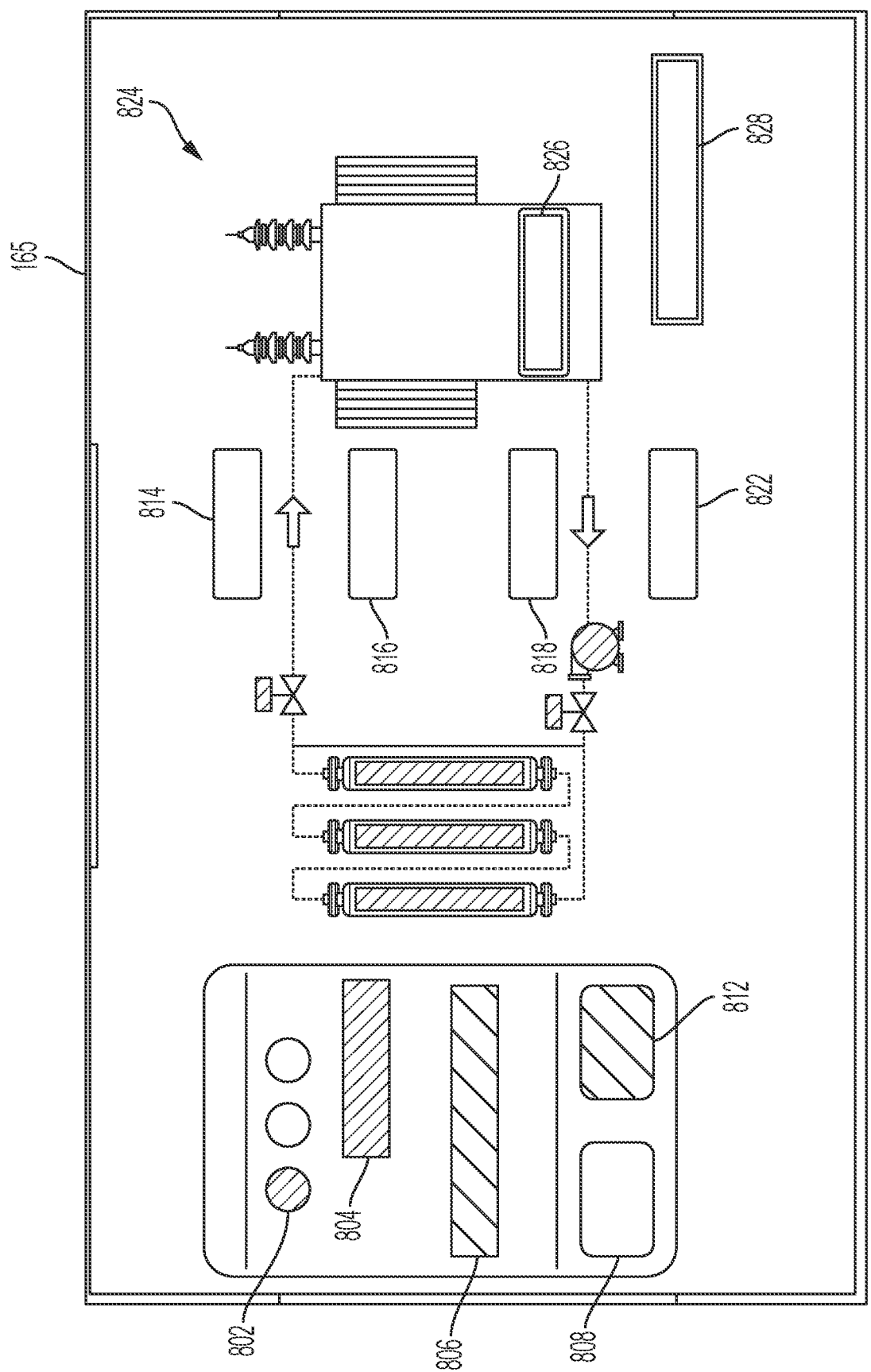
FIG. 8 is a diagram of a graphic user interface (GUI) illustrating data received from an incoming oil moisture and temperature sensor, outgoing oil moisture and temperature sensor, and processor, according to an embodiment.

For example, as illustrated in FIG. 8, the GUI 165, whether positioned locally at the moisture removal system 120, remotely from the moisture removal system 120, or both, may be configured to display data including any combination of: current system status 802, pump status 804, paper moisture level 806, alarm control functions 808, and pump control functions 812. In the embodiment illustrated in FIG. 8, the pump 135 may be operating normally, such that the current system status 802 may be displayed as "green" or otherwise positive, and the pump status 804 may indicate the pump 135 is running. In the embodiment illustrated in FIG. 8, the estimated paper moisture level 826, calculated or determined by the processor 145 may be high, and this status may be reflected in the paper moisture level 806 with the word "high," a "red" color, or other appropriate indication. The GUI 165 display may also include a visual diagram 824 of the moisture removal system 120, indicating a flow channel of the oil either through the drying cylinders 155a, 155b, 155c, or bypassing the drying cylinders 155a, 155b, 155c as appropriate based on the calculated estimated paper moisture level. In the illustrated embodiment, because the estimated paper moisture level 826 may be high 806, the GUI 165 display 824 may illustrate the oil flow channel through the drying cylinders, also indicated by the cycle indicator 828 listing the cycle as "active," and may include a display of the incoming oil temperature 818, incoming oil moisture level 822, outgoing oil temperature 816, and outgoing oil moisture level 814, as measured by the incoming oil moisture and temperature sensor 140 and outgoing oil moisture and temperature sensor 160, respectively. Personnel viewing this GUI 165 display may thus be able to visually track current system status and moisture levels in real time.

Figure 9:
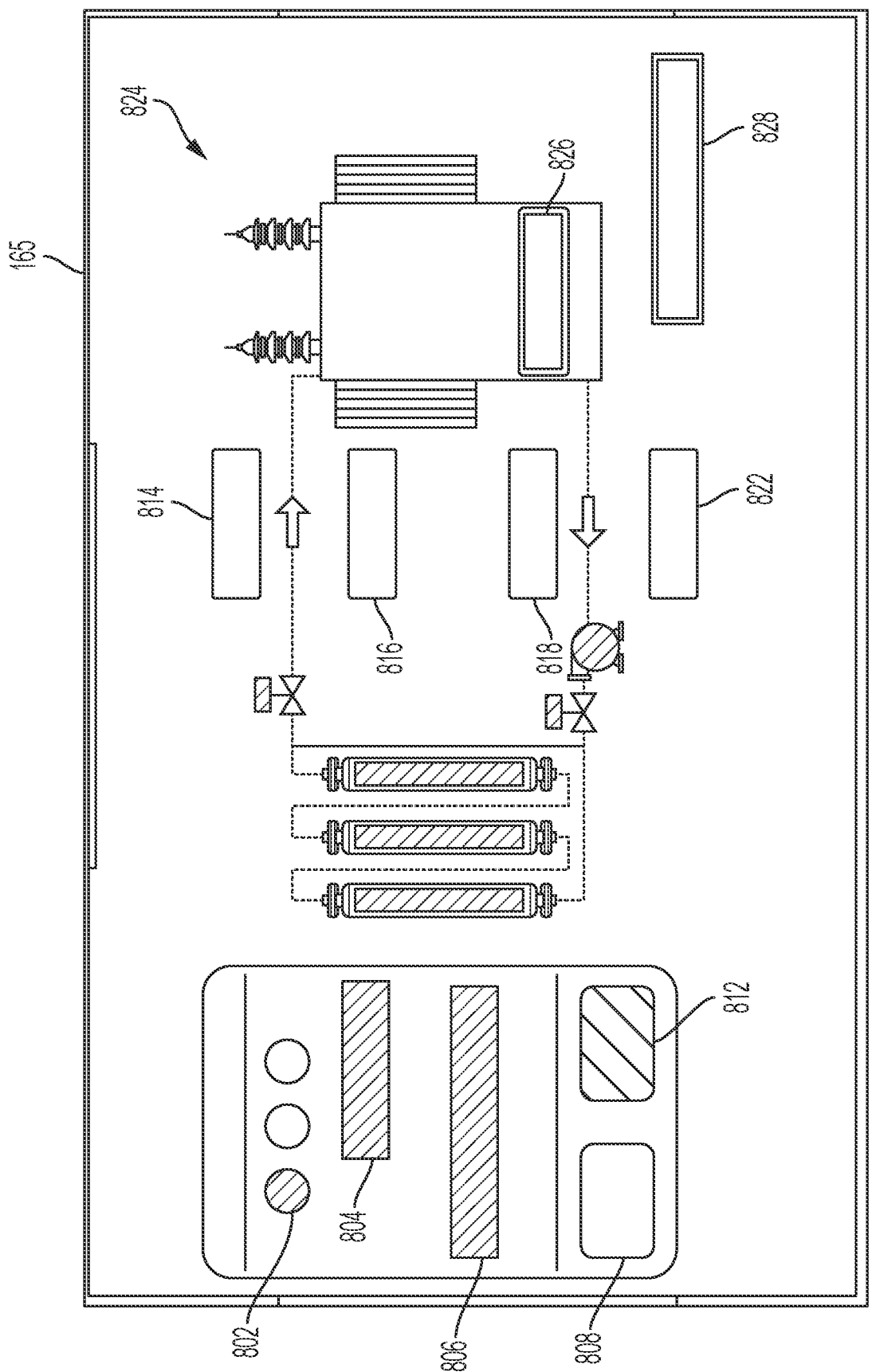
FIG. 9 is a diagram of a graphic user interface (GUI) illustrating data received from an incoming oil moisture and temperature sensor, outgoing oil moisture and temperature sensor, and processor, according to another embodiment.

FIG. 9 illustrates an alternate scenario, according to an embodiment, in which the oil has been flowing through the drying cylinders 155a, 155b, 155c, but the processor 145 has now determined that the estimated paper moisture level may create less risks, such that further drying is unnecessary, as will be understood by those skilled in the art. The GUI 165 in this scenario may display that the current system status 802 may be operable or "green," the pump status 804 is "running," and the paper moisture level 806 includes an indicator (for example, displayed as "low") to indicate that paper moisture level 806 is low, but not overdry. Further, such an indicator may indicate that there is relatively low risk of moisture causing paper deterioration and/or degradation, thus reducing risk of failure. The visual diagram 824 of the moisture removal system 120 may illustrate the flow channel of the oil through the drying cylinders 155a, 155b, 155c, and the incoming and outgoing oil moisture level and temperature indicators 814, 816, 818, 822 may indicate that the incoming and outgoing oil has a constant oil moisture level and temperature.

Figure 10:
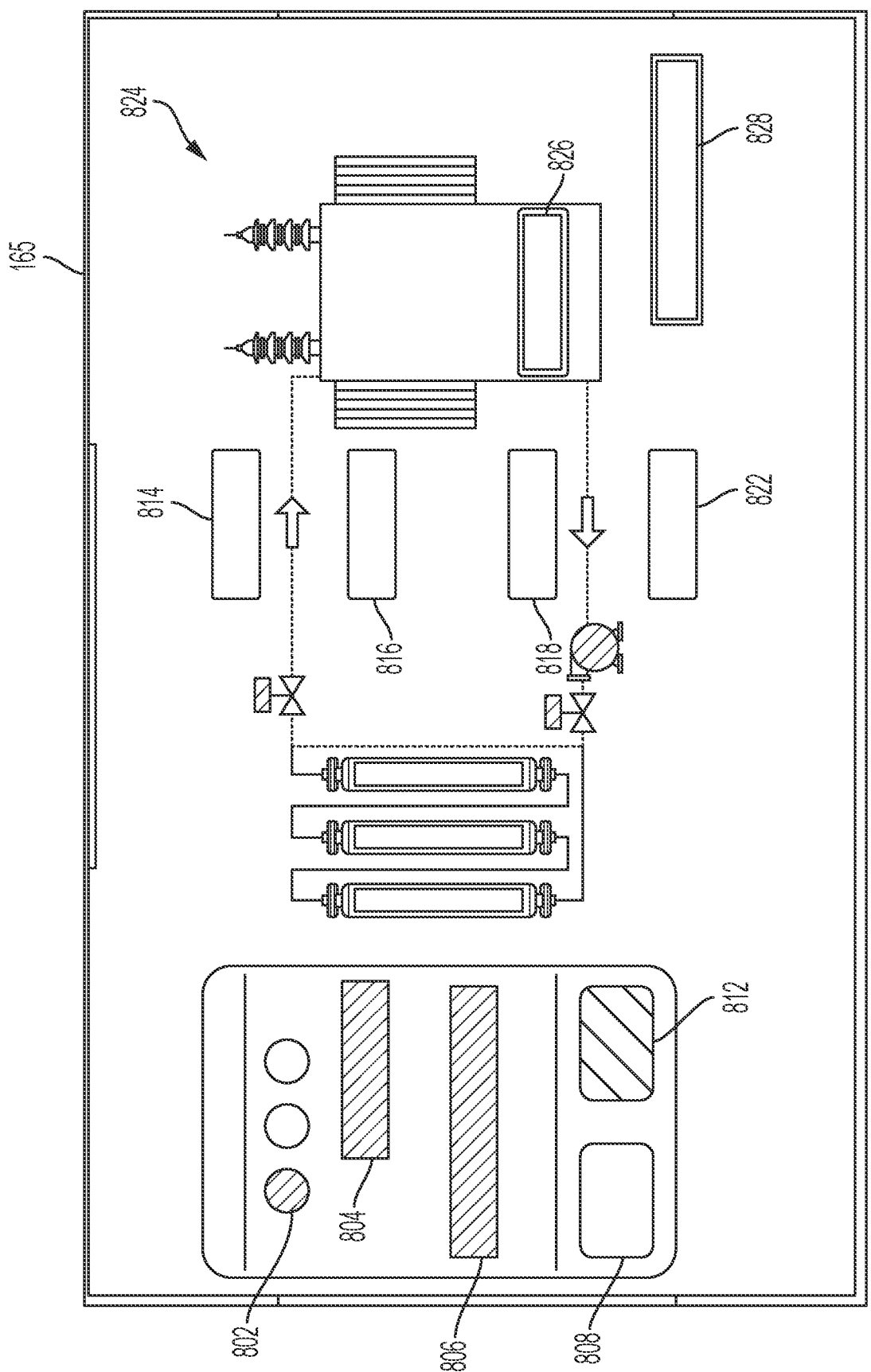
FIG. 10 is a diagram of a graphic user interface (GUI) illustrating data received from an incoming oil moisture and temperature sensor, outgoing oil moisture and temperature sensor, and processor, according to another embodiment.

In FIG. 10, an embodiment is illustrated in which, after having determined that the estimated paper moisture level 806 is low, but not overdry (e.g., displayed as "low"), the cycle mode 828 may be switched to "bypass" to avoid any overdrying. In this scenario, the GUI 165 may display the current system status 802 as operable or "green," the pump status 804 as "running," and the paper moisture level 806 as low, but not overdry (e.g., displayed as "low"). The visual diagram 824 of the moisture removal system 120 may illustrate the flow channel of the oil bypassing the drying cylinders 155a, 155b, 155c so as to exit the moisture removal system 120 without drying. The incoming and outgoing oil moisture level and temperature indicators 814, 816, 818, 822 may indicate that the incoming and outgoing oil has a constant oil moisture level and temperature.

Figure 11:
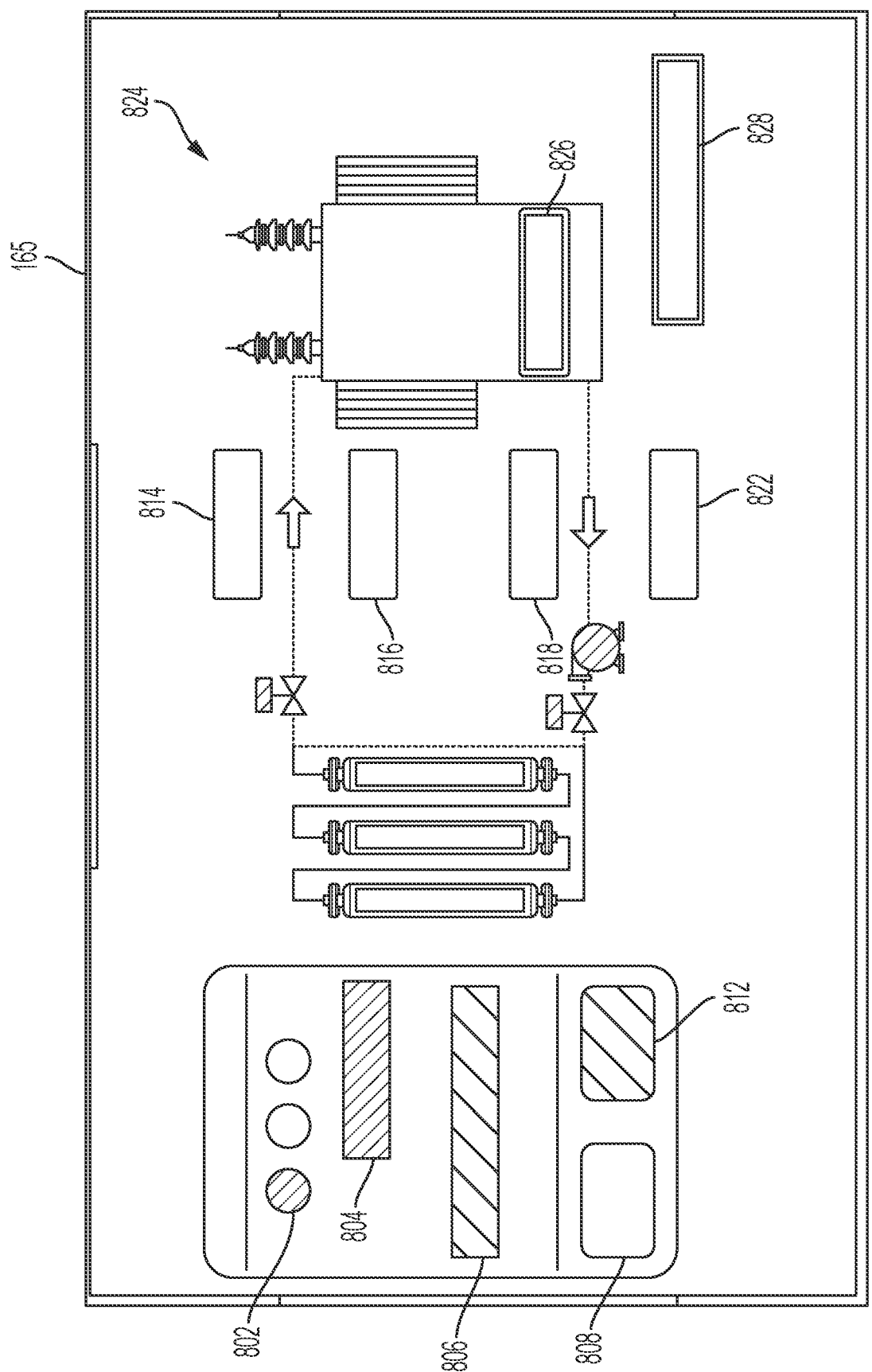
FIG. 11 is a diagram of a graphic user interface (GUI) illustrating data received from an incoming oil moisture and temperature sensor, outgoing oil moisture and temperature sensor, and processor, according to another embodiment.

In the embodiment illustrated in FIG. 11, the cycle mode 828 may have been in "bypass," but the incoming oil moisture and temperature sensors 140 may have detected an increase in the oil moisture level and/or percent relative saturation, and the processor 145 may have determined, based on that data, that the estimated paper moisture level 806 may now be "high." The GUI 165 may display this data, as the system prepares to switch to active mode so as to channel the high-moisture oil back through the drying cylinders 155a, 155b, 155c.

Personnel may use the data displayed on the GUI 165, locally at the moisture removal system 120 or remotely from the moisture removal system 120, or a combination thereof, to track the current cycle status, estimated paper moisture level, pump status, and the like, and take action to issue commands to the system as needed.

Figure 12:
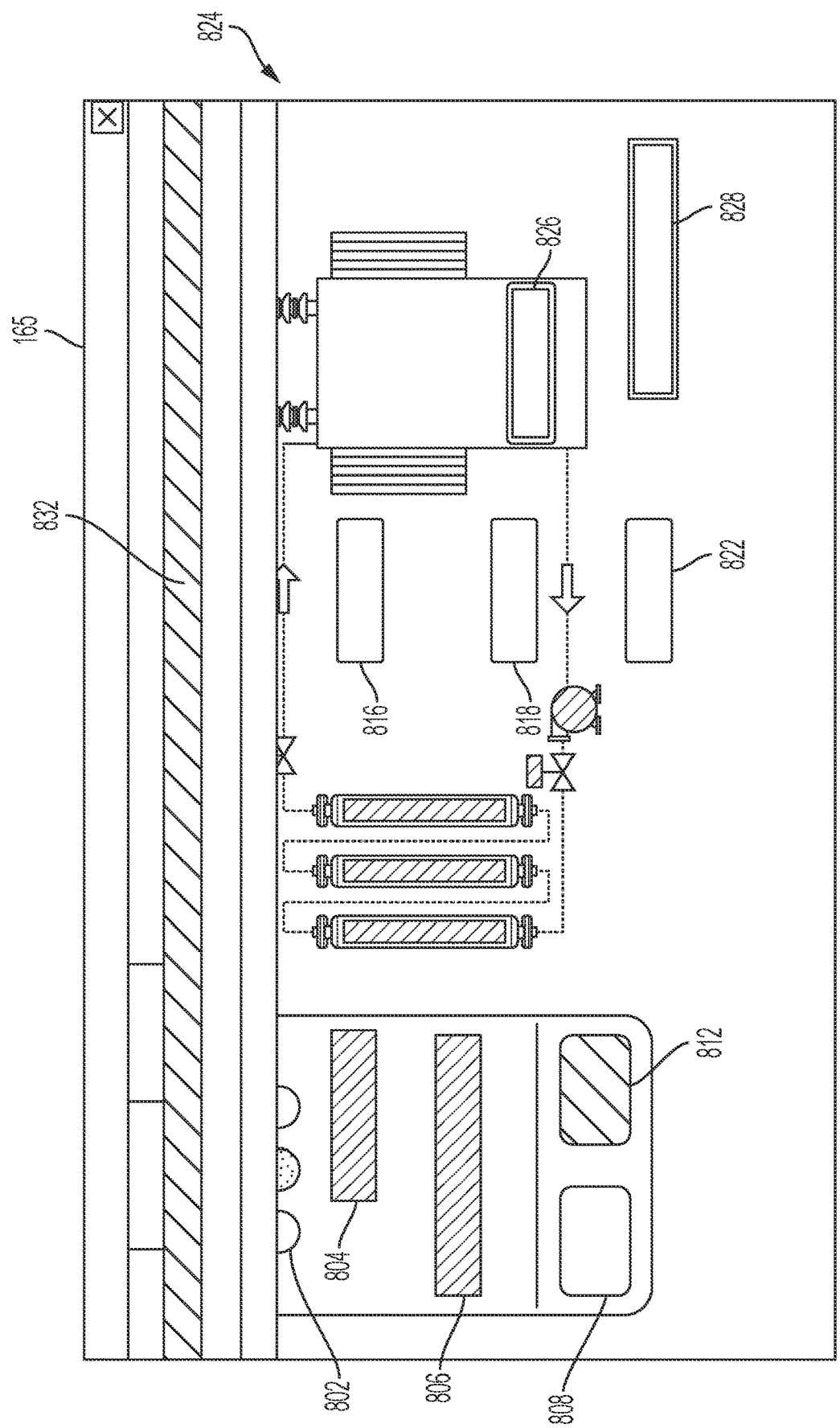
FIG. 12 is a diagram of a graphic user interface (GUI) illustrating data received from an incoming oil moisture and temperature sensor, outgoing oil moisture and temperature sensor, and processor, according to another embodiment.

In some examples, the GUI 165 may display alerts or alarm conditions, based on data received and processed by the processor 145. For example, as illustrated in FIG. 12, the GUI 165 may display an alarm condition 832 indicating that the drying cylinders 155a, 155b, 155c are saturated. This alarm condition 832 may be triggered based on a determination, by the processor 145, that the second moisture level and/or second percent relative saturation of the outgoing oil, as measured by the outgoing oil moisture and temperature sensor 160, may be equal to or greater than the first moisture level and/or first percent relative saturation of the incoming oil, as measured by the incoming oil moisture and temperature sensors 140. The values may be displayed by the incoming and outgoing oil moisture level and temperature indicators 814, 816, 818, 822 and/or percent relative saturation of the incoming and outgoing oil, and may provide personnel with data and information needed to take action to replace the drying cylinders 155a, 155b, 155c, or the drying agent therein.

Figure 13:
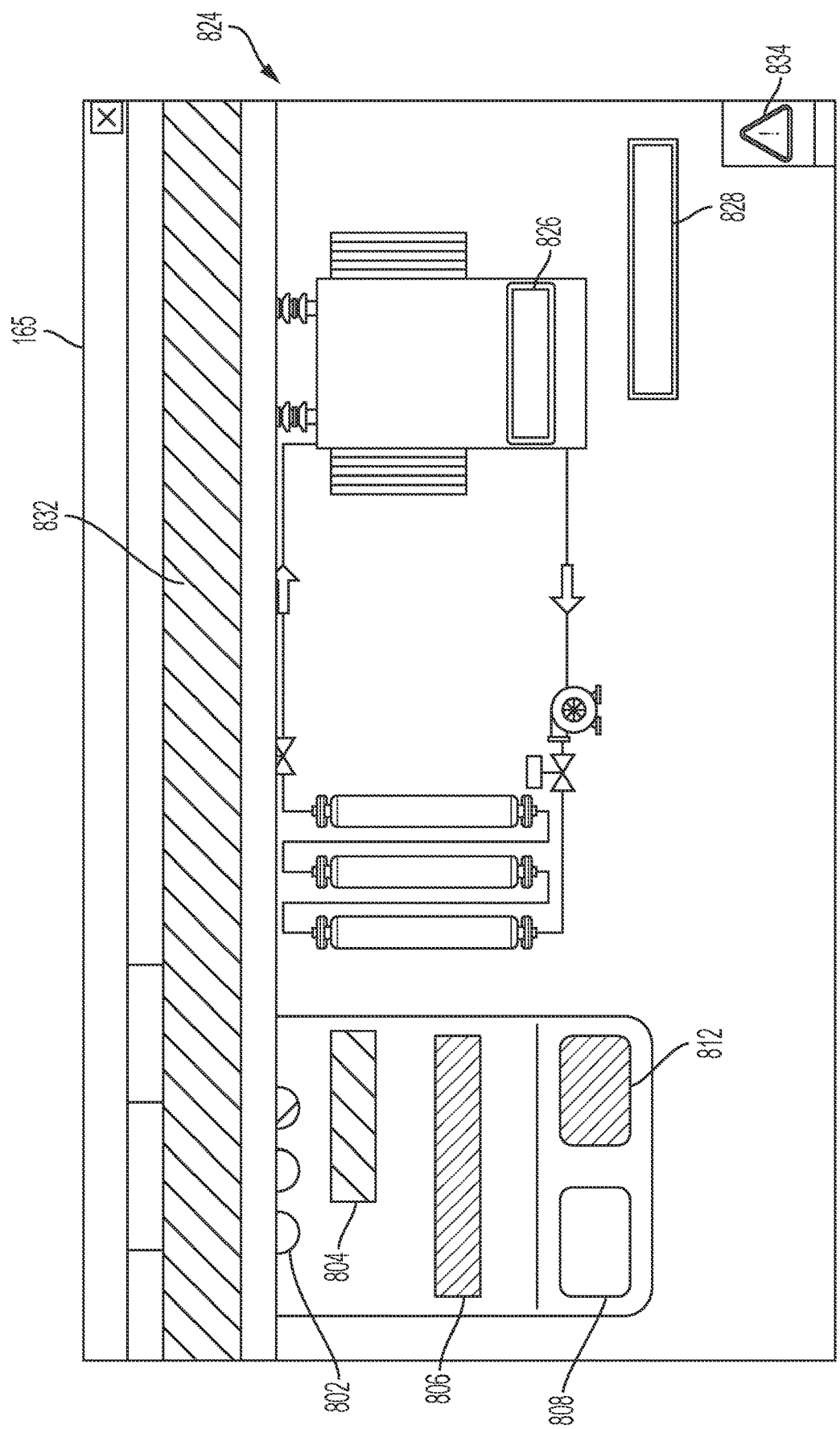
FIG. 13 is a diagram of a graphic user interface (GUI) illustrating data received from an incoming oil moisture and temperature sensor, outgoing oil moisture and temperature sensor, and processor, according to another embodiment.

In another embodiment, illustrated in FIG. 13, the GUI 165 may display an alert 834 and an alarm condition 832 indicating that low oil flow has been detected. In this scenario, the processor 145 may be configured to automatically shut off the moisture removal system 120 by stopping the pump 150 and isolating the moisture removal system 120 from the electric power transformer 110 so as to avoid damage to either the moisture removal system 120 or the electric power transformer 110. Various other alarms, alerts, and system operation GUI 165 displays are contemplated according to other embodiments, as will be readily understood by one of ordinary skill in the art, so as to enable personnel to view real time system information.

An embodiment of a system to remove moisture from a power transformer may also include a power transformer electrically connected to an electric grid. The power transformer may have cellulose paper insulation, for example, positioned therein and having oil running therethrough. The embodiment may also include a moisture removal system fluidly connected to the power transformer at an input channel and an output channel and positioned to move the oil from and to the power transformer. The moisture removal system, for example, may include a pump positioned so as to move oil from the power transformer into and through the moisture removal system through the input channel from the power transformer and return to the power transformer through the output channel, an internal moisture removal conduit fluidly connected to the input channel to receive the oil therefrom and fluidly connected to the output channel to return oil thereto, the internal moisture removal conduit including a first internal conduit path and a second internal conduit path, one or more drying cylinders fluidly connected to the first internal conduit path to reduce moisture content of the oil when flowing therethrough, one or more incoming oil moisture and temperature sensors positioned so as to detect moisture level, percent relative saturation, and/or temperature of the oil when pumped from the power transformer into the moisture removal system through the input channel, and a controller positioned to receive the detected moisture level, percent relative saturation, and/or temperature from the incoming oil moisture and temperature sensors. The controller may, responsive to the detected moisture level, percent relative saturation, and temperature, determine an estimated paper moisture value of the cellulose paper insulation and compare the determined estimated paper moisture value to a preselected target paper moisture value. The moisture removal system further may include an overdry prevention bypass valve responsive to the controller to direct the flow of the oil between the first internal conduit path and the second internal conduit path and positioned so as to allow the oil to circulate through the first internal conduit path to the one or more drying cylinders to reduce moisture content in the oil and to the output channel therefrom when the estimated paper moisture value may be greater than the preselected target paper moisture value and to divert oil through the second internal conduit path directly to the output channel without substantively reducing the moisture content in the oil when the estimated paper moisture value may be equal to or less than the preselected target paper moisture value. In an example, the system and controller may utilize a supervisory control and data acquisition (SCADA) architecture.

Figure 14:
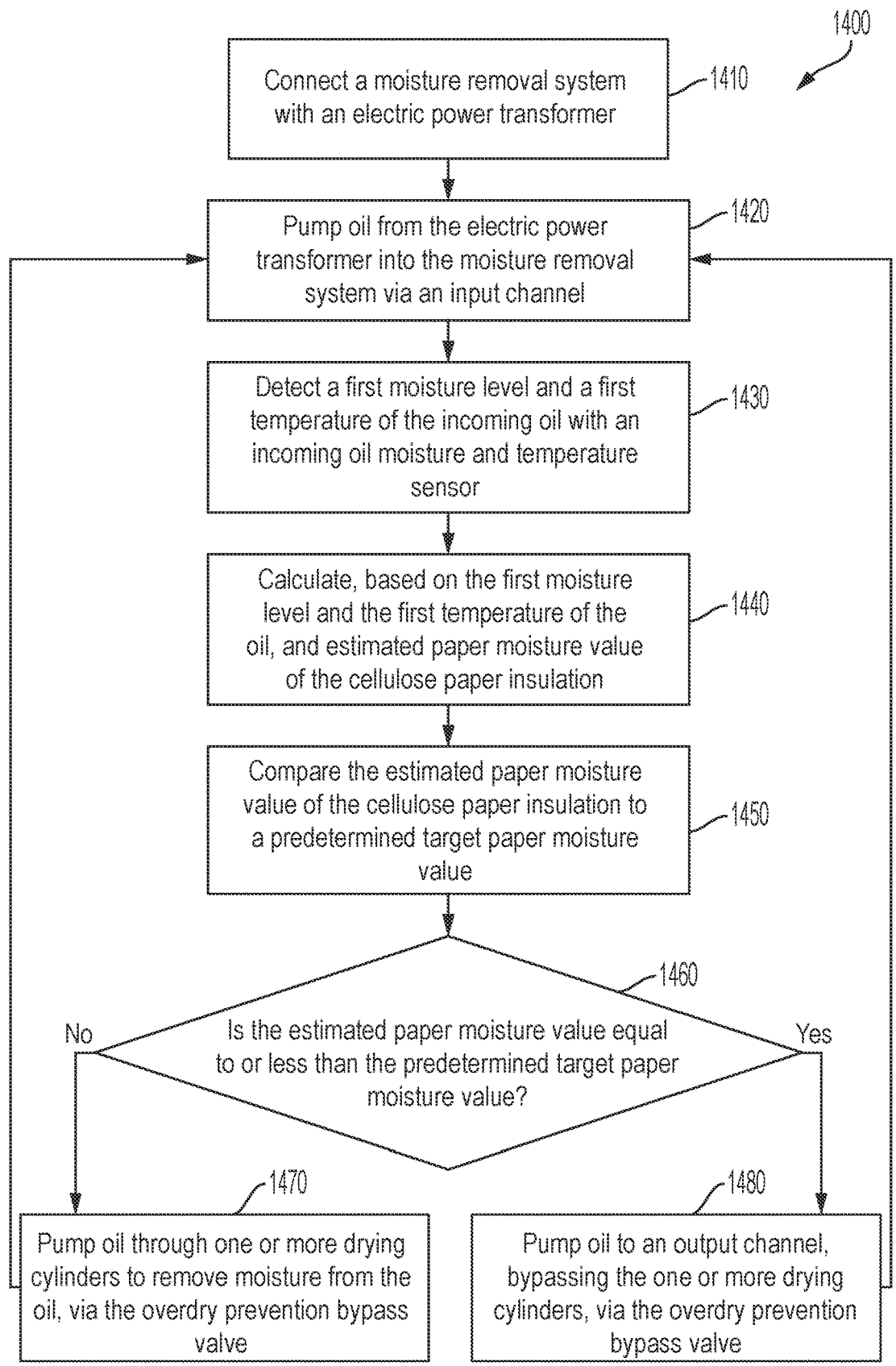
FIG. 14 is a flow chart illustrating a method for removing moisture from an electric power transformer, according to an embodiment.

FIG. 14 illustrates a method 1400 for removing moisture from an electric power transformer, according to an embodiment. At step 1410, the method 1400 may include fluidly connecting a moisture removal system with an electric power transformer at an input channel and an output channel, the electric power transformer electrically connected to an electric grid and having a plurality of cellulose paper insulation therein and oil running therethrough. At step 1420, the method 1400 may include pumping oil from the electric power transformer into the moisture removal system via the input channel. At step 1430, the method 1400 may include detecting a first moisture level and a first temperature of the incoming oil with one or more incoming oil moisture and temperature sensors. At step 1440, the method 1400 may include calculating or determining, via a processor, an estimated paper moisture value of the cellulose paper insulation based at least in part on the detected first moisture level and the first temperature of the incoming oil. At step 1450, the method 1400 may include comparing, via the processor, the estimated paper moisture value to a predetermined target paper moisture value. At step 1460, the method may include determining whether the estimated paper moisture value may be equal to or less than the predetermined target paper moisture value. If the processor determines that the estimated paper moisture value may be not equal to or less than the predetermined target paper moisture value—in other words, that the estimated paper moisture value may be greater than the predetermined paper moisture value—the method 1400 moves to step 1470, in which the oil is pumped through one or more drying cylinders to remove moisture from the oil, via the overdry prevention bypass valve. In the alternative, if the processor determines that the estimated paper moisture value may be equal to or less than the predetermined target paper moisture value, the method 1400 moves to step 1480, in which the oil is pumped to an output channel, bypassing the one or more drying cylinders, via the overdry prevention bypass valve. In either scenario, after passing through the one or more drying cylinders or bypassing the one or more drying cylinders, the oil will be returned to the electric power transformer, and additional oil from the electric power transformer will continue to pump into the moisture removal system, such that the method 1400 continues again at step 1420. In this way, the moisture removal system may continuously receive and channel oil from the electric power transformer based on continuous measurements of the oil moisture level and temperature, and calculations or determinations of the estimated paper moisture value based on the same.

Figure 15:
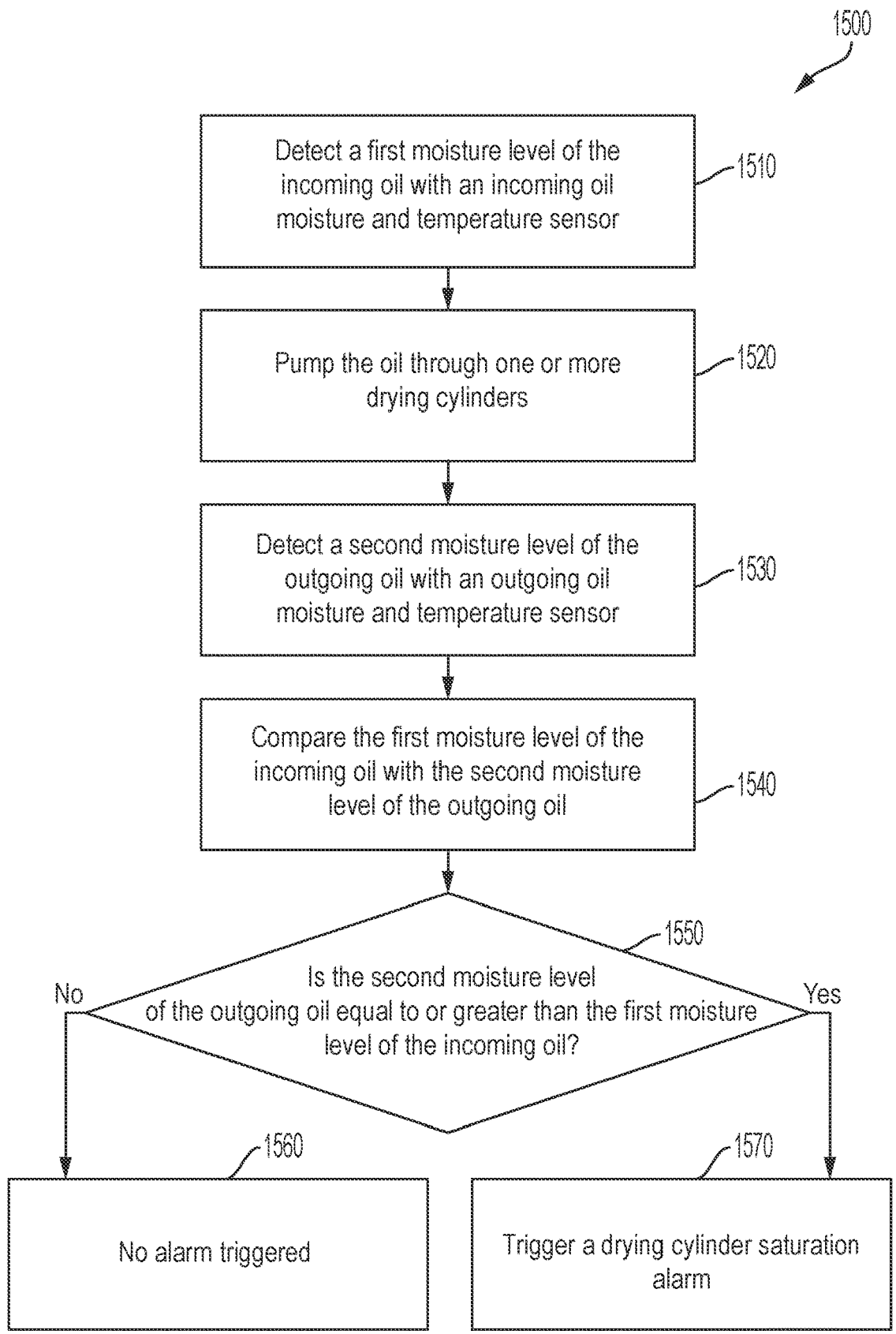
FIG. 15 is a flow chart illustrating a method for detecting drying cylinder saturation in a moisture removal system, according to an embodiment.

In the embodiment illustrated in FIG. 15, a method 1500 for detecting drying cylinder saturation is shown. As the moisture removal system operates continuously to remove moisture from the incoming oil, the moisture removal granules in the drying cylinders may become saturated such that they cease to be usable. In this case, the system may provide an alert to personnel to replace the granules or cylinders. For example, the method 1500 may include, at step 1510, detecting a first moisture level of the incoming oil with an incoming oil moisture and temperature sensor. Step 1520 may include pumping the oil through the one or more drying cylinders. At step 1530, the method 1500 may include detecting a second moisture level of the outgoing oil with an outgoing oil moisture and temperature sensor after the oil passes through the one or more drying cylinders. At step 1540, the method 1500 may include comparing the first moisture level of the incoming oil with the second moisture level of the outgoing oil. At step 1550, the method 1500 may include determining whether the second moisture level of the outgoing oil may be equal to or greater than the first moisture level of the incoming oil. If the processor determines that the second moisture level of the outgoing oil may be equal to or greater than the first moisture level of the incoming oil, that is an indication that the drying cylinders are no longer operating to remove moisture from the oil as it passes through the drying cylinders. Based on this determination at step 1550, a drying cylinder saturation alarm is triggered at step 1570, alerting personnel of the saturation. In the alternative, if the processor determines at step 1550 that the second moisture level of the outgoing oil is not equal to or greater than the first moisture level of the incoming oil—in other words, that the moisture level of the outgoing oil is less than the moisture level of the incoming oil—that may be an indication that the drying cylinders are operating properly to remove moisture from the oil, and no alarm is triggered at step 1560. This process according to method 1500 may operate continuously such that the saturation status of the drying cylinders may be constantly monitored and personnel may be alerted in real time to saturation conditions. In response to an alert that a drying cylinder is saturated, personnel may remove (e.g., to de-saturate or replace the zeolite granules) or replace the saturated drying cylinder. In such examples, the drying cylinder may be removed while the moisture removal system continues to operate and/or the electric power transformer continues to operate and remain energized. In other examples, an electric power transformer may be de-energized prior to removing or replacing a drying cylinder.

This application is a continuation of U.S. Non-Provisional application Ser. No. 17/072,275, filed Oct. 16, 2020, titled "SYSTEMS AND METHODS FOR REMOVING MOISTURE FROM A POWER TRANSFORMER," which claims the benefit of and priority to U.S. Provisional Application No. 62/956,400, filed Jan. 2, 2020, titled "SYSTEMS AND METHODS FOR REMOVING MOISTURE FROM A POWER TRANSFORMER," the entire disclosures of which are incorporated herein by reference.

In the drawings and specification, several embodiments of systems and methods to remove moisture from an electric power transformer have been disclosed, and although specific terms are employed, the terms are used in a descriptive sense only and not for purposes of limitation. Embodiments of systems and methods have been described in considerable detail with specific reference to the illustrated embodiments. However, it will be apparent that various modifications and changes may be made within the spirit and scope of the embodiments of systems and methods as described in the foregoing specification, and such modifications and changes are to be considered equivalents and part of this disclosure.

The invention claimed is:

1. A moisture removal system for removing moisture from a power transformer, the moisture removal system comprising:
   an input channel positioned to remove incoming oil received from the power transformer when the power transformer is positioned in fluid communication with the moisture removal system, the power transformer having cellulose paper insulation and oil positioned therein;
   a pump to move oil from the power transformer into and through the moisture removal system via the input channel when connected to the power transformer;
   one or more incoming oil moisture and temperature sensors to detect a first moisture level and a first temperature when oil is pumped from the power transformer into the moisture removal system via the input channel;
   a processor to receive the first moisture level and the first temperature from the one or more incoming oil moisture and temperature sensors, the processor configured to determine, based on the first moisture level and the first temperature, an estimated paper moisture value of the cellulose paper insulation, and further configured to compare the estimated paper moisture value to a predetermined target paper moisture value;
   an output channel to return oil from the moisture removal system to the power transformer when connected thereto; and
   an overdry prevention bypass valve configured in a first position so as to divert oil to the output channel without drying when the processor determines, based on the comparing, that the estimated paper moisture value is equal to or less than the predetermined target paper moisture value, and in a second position so as to channel oil through one or more drying cylinders so as to remove moisture from the oil when the processor determines, based on the comparing, that the estimated paper moisture value exceeds the predetermined target paper moisture value.

2. The moisture removal system of claim 1, further comprising:
an outgoing oil moisture and temperature sensor to detect a second moisture level and a second temperature of oil when passed through the one or more drying cylinders before returning to the power transformer via the output channel,
wherein the processor is configured to compare the first moisture level of the incoming oil with the second moisture level of the outgoing oil, and
wherein the processor is configured to trigger a drying cylinder saturation indication when the second moisture level of the outgoing oil is determined to be equal to or greater than the first moisture level of the incoming oil.

3. The moisture removal system of claim 2, wherein the one or more incoming oil moisture and temperature sensors and the outgoing oil moisture and temperature sensor are configured to detect each of the first moisture level, the second moisture level, the first temperature, and the second temperature on a continuous basis.

4. The moisture removal system of claim 2, further comprising:
a graphic user interface (GUI) connected to the one or more incoming oil moisture and temperature sensors, the outgoing oil moisture and temperature sensor, and the processor, the GUI configured to display data received from each of the one or more incoming oil moisture and temperature sensor, the outgoing oil moisture and temperature sensor, and the processor.

5. The moisture removal system of claim 4, wherein the GUI is selected from one or more of:
a GUI positioned on the moisture removal system and directly connected to the one or more incoming oil moisture and temperature sensor, the outgoing oil moisture and temperature sensor, and the processor, or
a GUI positioned remotely from the moisture removal system and wired or wirelessly connected to the one or more incoming oil moisture and temperature sensors, the outgoing oil moisture and temperature sensor, and the processor via a remote network.

6. The moisture removal system of claim 4, wherein the GUI is configured to:
receive an input at the GUI, and
communicate, via the processor, a command to move the overdry prevention bypass valve to one of the first position and the second position based on the received input.

7. The moisture removal system of claim 1, wherein the one or more drying cylinders comprise zeolite granules to capture water moisture molecules from the oil as the oil passes through the one or more drying cylinders.

8. The moisture removal system of claim 1, wherein the moisture removal system comprises a kit to be added to or removed from the power transformer.

9. The moisture removal system of claim 1,
wherein the one or more incoming oil moisture and temperature sensors to detect a first percent saturation level of oil when pumped from the power transformer,
wherein the processor further receives the first percent saturation level from the one or more incoming oil moisture and temperature sensors, and wherein the processor is configured to determine, further based on the first percent saturation level, the estimated paper moisture value of the cellulose paper insulation.

10. A system for removing moisture from a power transformer, the system comprising:
a power transformer electrically connected to an electric grid, the power transformer having cellulose paper insulation and oil positioned therein; and
a moisture removal system connected to the power transformer at an input channel and an output channel, the moisture removal system comprising:
a pump positioned so as to move oil from the power transformer into and through the moisture removal system via the input channel,
one or more incoming oil moisture and temperature sensors to detect a first moisture level and a first temperature of oil when pumped from the power transformer into the moisture removal system via the input channel,
a processor to receive the first moisture level and the first temperature from the one or more incoming oil moisture and temperature sensors, the processor configured to determine, based on the first moisture level and the first temperature, an estimated paper moisture value of the cellulose paper insulation, and further configured to compare the estimated paper moisture value to a predetermined target paper moisture value, and
an overdry prevention bypass valve configured in a first position so as to divert oil to the output channel without drying when the processor determines, based on the comparing, that the estimated paper moisture value is equal to or less than the predetermined target paper moisture value, and in a second position so as to channel oil through one or more drying cylinders so as to remove moisture from the oil when the processor determines, based on the comparing, that the estimated paper moisture value exceeds the predetermined target paper moisture value.

11. The system of claim 10, further comprising:
an outgoing oil moisture and temperature sensor, positioned so as to detect a second moisture level and a second temperature of oil that has passed through the one or more drying cylinders before returning to the power transformer via the output channel;
wherein the processor is configured to compare the first moisture level of the incoming oil with the second moisture level of the outgoing oil; and
wherein the processor is configured to trigger a drying cylinder saturation alarm when the second moisture level of the outgoing oil is determined to be equal to or greater than the first moisture level of the incoming oil.

12. The system of claim 11, wherein the one or more incoming oil moisture and temperature sensors and the outgoing oil moisture and temperature sensor are configured to detect each of the first moisture level, the second moisture level, the first temperature, and the second temperature on a continuous basis.

13. The system of claim 11, further comprising:
a graphic user interface (GUI) connected to the one or more incoming oil moisture and temperature sensors, the outgoing oil moisture and temperature sensor, and the processor, the GUI configured to display data received from each of the one or more incoming oil moisture and temperature sensors, the outgoing oil moisture and temperature sensor, and the processor.

14. The system of claim 13, wherein the GUI is selected from one or more of:
a GUI positioned on the moisture removal system and directly connected to the one or more incoming oil moisture and temperature sensors, the outgoing oil moisture and temperature sensor, and the processor, or
a GUI positioned remotely from the moisture removal system and wired or wirelessly connected to the one or more incoming oil moisture and temperature sensor, the outgoing oil moisture and temperature sensor, and the processor via a remote network.

15. The system of claim 13, wherein the GUI is configured to:
receive input, and
communicate, via the processor, a command to move the overdry prevention bypass valve to one of the first position and the second position based on the received input.

16. The system of claim 10, wherein the one or more drying cylinders comprise zeolite granules to capture water moisture molecules from the oil as the oil passes through the one or more drying cylinders.

17. A system to remove moisture from a power transformer, the system comprising:
a power transformer having cellulose paper insulation and oil positioned therein; and
a moisture removal system connected to the power transformer and positioned to move the oil from and to the power transformer, the moisture removal system including:
a pump positioned to move oil from the power transformer into and through the moisture removal system from the power transformer and return to the power transformer therefrom,
an internal moisture removal conduit to receive the oil and return oil thereto, the internal moisture removal conduit including a first internal conduit path and a second internal conduit path,
one or more drying cylinders fluidly connected to the first internal conduit path to reduce moisture content of the oil when flowing therethrough,
one or more incoming oil moisture and temperature sensors positioned to detect moisture level and temperature of the oil when pumped from the power transformer into the moisture removal system,
a controller positioned to receive the detected moisture level and temperature from the one or more incoming oil moisture and temperature sensors, the controller being responsive to the detected moisture level and temperature to determine an estimated paper moisture value of the cellulose paper insulation and to compare the determined estimated paper moisture value to a preselected target paper moisture value, and
an overdry prevention bypass valve responsive to the controller to direct the flow of the oil between the first internal conduit path and the second internal conduit path and positioned so as to allow the oil to circulate through the first internal conduit path to the one or more drying cylinders to reduce moisture content in the oil and to the output channel therefrom and to divert oil through the second internal conduit path directly to the output channel.

18. A method for removing moisture from a power transformer, the method comprising:
connecting a moisture removal system with a power transformer at an input channel and an output channel, the power transformer having cellulose paper insulation and oil therein;
pumping oil from the power transformer into the moisture removal system via the input channel;
detecting a first moisture level and a first temperature of the incoming oil;
determining, via a processor, an estimated paper moisture value of the cellulose paper insulation based at least in part on the detected first moisture level and the first temperature of the incoming oil;
comparing, via the processor, the estimated paper moisture value to a predetermined target paper moisture value; and
positioning, via the processor, an overdry prevention bypass valve based at least on the comparing, the overdry prevention bypass valve configured to channel the incoming oil through one or more drying cylinders positioned to remove moisture from the oil when the estimated paper moisture value is determined to be greater than the predetermined target paper moisture value, and configured to divert the incoming oil to bypass the one or more drying cylinders when the estimated paper moisture value is determined to be less than or equal to the predetermined target paper moisture value.

19. The method of claim 18, the method further comprising:
detecting a second moisture level of the outgoing oil after the oil passes through the one or more drying cylinders;
comparing, via the processor, the first moisture level of the incoming oil with the second moisture level of the outgoing oil;
determining, via the processor, that second moisture level of the outgoing oil is equal to or greater than the first moisture level of the incoming oil; and
triggering a drying cylinder saturation indication, via the processor, based at least in part on the determining.

20. The method of claim 19, further comprising detecting each of the first moisture level, the second moisture level, the first temperature, and the second temperature on a continuous basis.

21. The method of claim 19, the method further comprising displaying data from the processor on a graphic user interface (GUI) connected to the processor, the displaying data on the GUI comprises one or more of:
displaying data at a GUI positioned on the moisture removal system and directly connected to the processor, or
displaying data at a GUI positioned remotely from the moisture removal system and wired or wirelessly connected to the processor via a remote network.

22. The method of claim 21, the method further comprising:
receiving an input at the GUI; and
communicating, via the processor, a command to move the overdry prevention bypass valve to one of the first position and the second position based on the received input.

23. The method of claim 18, further comprising:
detecting a low oil flow; and
isolating the moisture removal system from the power transformer in response to the detecting the lower oil flow.

* * * * *